US012773456B2

(12) United States Patent
Schiffman et al.

(10) Patent No.: US 12,773,456 B2
(45) Date of Patent: Oct. 27, 2026

(54) DRUG DELIVERY SYSTEMS COMPRISING A NEUROTROPHIC AGENT, AN APOPTOSIS SIGNALING FRAGMENT INHIBITOR (FAS) OR FAS LIGAND (FASL) INHIBITOR, A TUMOR NECROSIS FACTOR-α (TNF-α) OR TNF RECEPTOR INHIBITOR, A MITOCHONDRIAL PEPTIDE, AN OLIGONUCLEOTIDE, A CHEMOKINE INHIBITOR, OR A CYSTEINE-ASPARTIC PROTEASE INHIBITOR

(71) Applicant: Cella Therapeutics, LLC, Miami, FL (US)

(72) Inventors: Rhett M. Schiffman, Laguna Beach, CA (US); Lukas Scheibler, Laguna Beach, CA (US)

(73) Assignee: Cella Therapeutics, LLC, Miami, FL (US)

( * ) Notice: Subject to any disclaimer, the term of this patent is extended or adjusted under 35 U.S.C. 154(b) by 0 days.

(21) Appl. No.: 19/238,317

(22) Filed: Jun. 13, 2025

(65) Prior Publication Data

US 2026/0041777 A1 Feb. 12, 2026

Related U.S. Application Data

(63) Continuation-in-part of application No. 18/893,848, filed on Sep. 23, 2024, which is a continuation of application No. 17/125,776, filed on Dec. 17, 2020, now Pat. No. 12,128,104, which is a continuation of application No. PCT/US2019/037791, filed on Jun. 18, 2019.

(60) Provisional application No. 62/687,173, filed on Jun. 19, 2018, provisional application No. 62/725,972, filed on Aug. 31, 2018, provisional application No. 62/747,575, filed on Oct. 18, 2018, provisional application No. 62/787,873, filed on Jan. 3, 2019.

(51) Int. Cl.

| | |
|---|---|
| ***A61K 38/08*** | (2019.01) |
| ***A61K 38/10*** | (2006.01) |
| ***A61K 45/06*** | (2006.01) |
| ***A61K 47/52*** | (2017.01) |
| ***A61K 47/60*** | (2017.01) |

(52) U.S. Cl.

CPC .............. *A61K 47/52* (2017.08); *A61K 38/08* (2013.01); *A61K 38/10* (2013.01); *A61K 45/06* (2013.01); *A61K 47/60* (2017.08)

(58) Field of Classification Search

CPC ........ A61K 47/52; A61K 38/08; A61K 38/10; A61K 45/06; A61K 47/60

See application file for complete search history.

(56) References Cited

U.S. PATENT DOCUMENTS

| | | | | |
|---|---|---|---|---|
| 8,338,378 | B2 | 12/2012 | Mossier et al. | |
| 8,592,374 | B2 * | 11/2013 | Mosler .................... | A61P 25/28 514/17.7 |
| 8,796,214 | B2 | 8/2014 | Iqbal et al. | |
| 8,796,215 | B2 | 8/2014 | Iqbal et al. | |
| 9,249,203 | B2 | 2/2016 | Iqbal et al. | |
| 9,327,011 | B2 | 5/2016 | Iqbal et al. | |
| 9,737,587 | B2 | 8/2017 | Iqbal et al. | |
| 12,128,104 | B2 * | 10/2024 | Schiffman .............. | A61K 45/06 |
| 2006/0246036 | A1 | 11/2006 | Francis et al. | |
| 2007/0184522 | A1 | 8/2007 | Zarnegar et al. | |
| 2010/0189765 | A1 | 7/2010 | Erickson et al. | |
| 2010/0226878 | A1 | 9/2010 | Zacks | |
| 2011/0160141 | A1 | 6/2011 | Mossier et al. | |
| 2012/0237473 | A1 | 9/2012 | Kolomeyer et al. | |
| 2013/0053328 | A1 | 2/2013 | Zacks et al. | |
| 2016/0346197 | A1 | 12/2016 | Goldberg et al. | |

FOREIGN PATENT DOCUMENTS

| | | | |
|---|---|---|---|
| CN | 102123713 | A | 7/2011 |
| CN | 104640568 | A | 5/2015 |
| CN | 112566622 | A | 3/2021 |
| CN | 112672732 | A | 4/2021 |
| JP | 2000511561 | A | 9/2000 |

(Continued)

OTHER PUBLICATIONS

International Search Report and Writien Opinion for PCT/US2019/037791, mailed Oct. 11, 2019.

Liu et al., Inhibition of AMO-Like Pathology With a Neurotrophic Compound in Aged Rats and 3xTg-AD Mice, Frontiers in Aging Neuroscience, vol. 11, Article 309, 1-18, Nov. 2019.

Cao et al., "Delivering neuroactive molecules from biodegradable microspheres for application in central nervous system disorders", ScienceDirect, https://www.sciencedirect.com/science/article/abs/pii/S0142961298001720?via%3Dihub, 3 pgs.

(Continued)

*Primary Examiner* — Ernst V Arnold

(74) *Attorney, Agent, or Firm* — Procopio, Cory, Hargreaves & Savitch LLP; Brent Johnson; Devang Thakor

(57) ABSTRACT

This disclosure relates to a drug delivery system comprising a neurotrophic agent, an apoptosis signaling fragment inhibitor (FAS) or FAS-ligand (FASL) inhibitor, a tumor necrosis factor-α (TNF-α) or TNF receptor (TNFR) inhibitor, a mitochondrial peptide, an oligonucleotide, a chemokine inhibitor, or a cysteine-aspartic protease (caspase) inhibitor, including any combination of these compounds and, optionally, a sustained delivery component. This type of drug delivery system can be used to treat a medical condition such as an inherited or age-related choroid, retina, optic nerve disorder, or optic nerve degeneration; an otic disorder; a neurologic or CNS disorder; or a related condition; or a condition related to occlusion or obstruction of a blood vessel or blood circulation such as a stroke, myocardial or renal infarction. Medicaments, methods of manufacturing medicaments, kits, and other related products or methods are also described.

19 Claims, No Drawings

Specification includes a Sequence Listing.

(56) References Cited

FOREIGN PATENT DOCUMENTS

| | | | |
|---|---|---|---|
| JP | 2001354697 | A | 12/2001 |
| JP | 2012519696 | A | 8/2012 |
| JP | 2018515582 | A | 6/2018 |
| WO | 0158494 | A2 | 8/2001 |
| WO | 2004050027 | A2 | 6/2004 |
| WO | 2009137085 | A2 | 11/2009 |
| WO | 2016094876 | A1 | 6/2016 |
| WO | 2019246130 | A1 | 12/2019 |
| WO | 2019246141 | A1 | 12/2019 |

OTHER PUBLICATIONS

Gillespie et al., "BDNF-induced survival of auditory neurons in vivo: Cessation of treatment leads to accelerated loss of survival effects", https://doi.org/10.1002/jnr.10542, Journal of Neuroscience Research, vol. 71, Issue 6, pp. 785-790, 2003.
Mohtaram et al., "Biomaterial-based drug delivery systems for the controlled release of neurotrophic factors", IOPscience, Published Feb. 5, 2013, Biomedical Materials, vol. 8, No. 2, https://iopscience.iop.org/article/10.1088/1748-6041/8/2/022001/meta, 6 pgs.
Yamagishi et al., "Pigment epithelium-derived factor inhibitsTNF-α-induced interleukin-6 expression in endothelial cells by suppressing NADPH oxidase-mediated reactive oxygen species generation", ScienceDirect, https://doi.org/10.1016/j.yjmcc.2004.04.007, Journal of Molecular and Cellular Cardiology, vol. 37, Issue 2, Aug. 2004, pp. 497-506.
Notice of Acceptance for patent application for Australian patent application No. 2022247731 dated Jan. 13, 2025, 3 pages.
Beech et al. "Neuroprotection in Ischemia-Reperfusion Injury: An Antiinflammatory Approach Using a Nobel Broad-Spectrum Chemoking Inhibitor" Journal of Cerebral Blood Flow and Metabolism, 21: 683-689. 2001.
Chang et al. "Tumor necrosis factor α Inhibition for Alzheimer's Disease" Journal of Central Nervous System Disease 2017; vol. 9:1-5.
Gong et al. "Humanin and age-related diseases: a new link?" Frontiers in Endocrinology, vol. 5, Article 210. Dec. 2014.
Khan et al. "Implication of Caspase-3 as a Common Therapeutic Target for Multineurodegenerative Disorders and Its Inhibition Using Nonpeptidyl Natural Compounds" BioMed Research International, vol. 2015, Article ID 379817, 9 pages, 2015.
Li et al., "Neurotrophic peptides incorporating adamantane improve learning and memory, promote neurogenesis and synpatic plasticity in mice" FEBS Letters, 2010, vol. 584, pp. 3359-3365.
Planells-Ferrer et al. "Fas apoptosis inhibitory molecules: more than death-receptor antagonists in the nervous system" Journal of Neurochemistry, Oct. 2016; 139(1):11-21.
Wall et al. "Are animal models as good as we think?" Theriogenology, 2008; 69:2-9.
Browne, C.D. et al., Inhibition of endothelial cell proliferation and angiogenesis by orlistat, a fatty acid synthase inhibitor, The FASEB Journal, vol. 20, 2027-2035, Oct. 2006.
Jiang et al., "HMGB1 release triggered by the interaction of live retinal cells and uveitogenic T cells is Fas/FasL activation-dependent", Journal of Neuroinflammation (2015) 12:179 DOI 10.1186/s12974-015-0389-2, 10 pgs.
Roberts et al., "Chemistry for peptide and protein PEGylation", Advanced Drug Delivery Reviews 54 (2002) 459-476.
Li et al., "Inhibition of Fas/FasL mRNA expression and TNF-α release in concanavalin A-induced liver injury in mice by bicycolo", World J Gastroenterol, 2004, vol. 10, No. 12, pp. 1775-1779.
Chohan et al., "Enhancement of dentate gyrus neurogenesis, dendritic and synaptic plasticity and memory by a neurotrophic peptide", Neurobiology of Aging 32 (2011) pp. 1420-1343.

* cited by examiner

DRUG DELIVERY SYSTEMS COMPRISING A NEUROTROPHIC AGENT, AN APOPTOSIS SIGNALING FRAGMENT INHIBITOR (FAS) OR FAS LIGAND (FASL) INHIBITOR, A TUMOR NECROSIS FACTOR-α (TNF-α) OR TNF RECEPTOR INHIBITOR, A MITOCHONDRIAL PEPTIDE, AN OLIGONUCLEOTIDE, A CHEMOKINE INHIBITOR, OR A CYSTEINE-ASPARTIC PROTEASE INHIBITOR

CROSS-REFERENCE TO RELATED APPLICATIONS

This application is a continuation-in-part of U.S. patent application Ser. No. 18/893,848, filed Sep. 23, 2024, which is a continuation of U.S. patent application Ser. No. 17/125,776, filed Dec. 17, 2020, which is a continuation of International Patent Application PCT/US2019/037791, filed Jun. 18, 2019, which claims the benefit of United States Provisional Application Nos. 62/687,173, filed Jun. 19, 2018, 62/725,972, filed Aug. 31, 2018, 62/747,575, filed Oct. 18, 2018, and 62/787,873, filed Jan. 3, 2019, all of which are incorporated by reference herein in their entireties. PCT/US19/37774, filed Jun. 18, 2019, is also incorporated by reference herein in its entirety.

SEQUENCE LISTING

The instant application contains a Sequence Listing which has been submitted electronically in XML format and is hereby incorporated by reference in its entirety. Said XML copy, created on May 20, 2026, is named 134145-0005CT03 v2.xml and is 24,449 bytes in size.

SUMMARY

This disclosure relates to a drug delivery system comprising a neurotrophic agent, an apoptosis signaling fragment inhibitor (FAS) or FAS-ligand (FASL) inhibitor, a tumor necrosis factor-α (TNF-α) or TNF receptor (TNFR) inhibitor, a mitochondrial peptide, an oligonucleotide, a chemokine inhibitor, or a cysteine-aspartic protease (caspase) inhibitor, including any combination of these compounds and, optionally, a sustained delivery component. This type of drug delivery system can be used to treat a medical condition such as an inherited or age-related choroid, retina, optic nerve disorder, or optic nerve degeneration; an otic disorder; a neurologic or CNS disorder; or a related condition; or a condition related to occlusion or obstruction of a blood vessel or blood circulation such as a stroke, myocardial or renal infarction.

Some embodiments include a drug delivery system comprising: a first active pharmaceutical ingredient (API) and a sustained delivery component, wherein the first API is a neurotrophic agent, a FAS/FASL inhibitor, a TNF-α/TNFR inhibitor, a mitochondrial peptide, a chemokine inhibitor, a cysteine-aspartic protease (caspase) or caspase inhibitor, or a combination thereof.

Some embodiments include a method of treating a medical condition comprising administering a drug delivery system of described herein to a mammal in need thereof, wherein the medical condition comprises: 1) an inherited or age-related choroid, retina, or optic nerve disorder or degeneration; 2) an otic disorder; or 3) a neurologic or CNS disorder.

Use of a FAS/FASL inhibitor, a TNF-α/TNFR inhibitor, a mitochondrial peptide, a chemokine inhibitor, a caspase inhibitor, or a combination thereof in the manufacture of a drug delivery system for the treatment of 1) an inherited or age-related choroid, retina, or optic nerve disorder or degeneration; 2) an otic disorder; or 3) a neurologic or CNS disorder, wherein the drug delivery system further comprises a sustained delivery component.

A kit comprising a drug delivery system of described herein and a label with instructions for use of the drug delivery system for the treatment of 1) an inherited or age-related choroid, retina, or optic nerve disorder or degeneration; 2) an otic disorder; or 3) a neurologic or CNS disorder.

DETAILED DESCRIPTION

With respect to a subject drug delivery system, a neurotrophic agent can include a CNTF compound or another neurotrophic agent, a CNTF compound includes any compound having a structure or activity similar to ciliary neurotrophic factor (CNTF), including CNTF, protein derivatives of CNTF, or a CNTF peptide. Examples include CNTF, a peptide containing part of the CNTF sequence, such as Peptide 6 (P6; Ac-VGDGGLFEKKL-NH2 (SEQ ID NO: 1)) and Peptide 21 (P21; Ac-DGGLAG-NH2 (SEQ ID NO: 2)), a peptide containing the amino acid sequence of SEQ ID NO: 18 (DGGL), recombinant CNTF (rhCNTF), or a neurotrophic peptide identified in U.S. Pat. No. 8,592,374, which is incorporated herein by reference for its disclosure related to neurotrophic peptides, including neurotrophic peptides having an adamantly group at the C- and/or N-terminal end, or any other peptide having similar biological activity to CNTF. Other neurotrophic agents include nerve growth factor (NGF), Brain-derived neurotrophic factor (BDNF), glial cell-derived neurotrophic factor (GDNF), etc.

Any suitable amount of a neurotrophic agent, such as a CNTF compound, NGF, BDNF, GDNF, etc., may be used in the drug delivery system. For example, a drug delivery system may contain about 0.01-1 μg, about 1-2 μg, about 2-3 μg, about 3-4 μg, about 4-5 μg, about 5-6 μg, about 6-7 μg, about 7-8 μg, about 8-9 μg, about 9-10 μg, about 0.01-3 μg, about 3-6 μg, about 6-10 μg, about 0.01-10 μg, about 10-20 μg, about 20-30 μg, about 30-40 μg, about 40-50 μg, about 50-60 μg, about 60-70 μg, about 70-80 μg, about 80-90 μg, about 90-100 μg, about 0.01-30 μg, about 30-60 μg, about 60-100 μg, about 0.01-100 μg, about 0.1-100 μg, about 100-200 μg, about 200-300 μg, about 300-400 μg, about 400-500 μg, about 500-600 μg, about 600-700 μg, about 700-800 μg, about 800-900 μg, about 900-1,000 μg, about 0.01-300 μg, about 300-600 μg, about 600-1,000 μg, about 0.01-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for a neurotrophic agent, such as a CNTF compound, NGF, BDNF, GDNF, etc., in a drug delivery system, may provide a drug delivery system that provides therapeutic levels of the neurotrophic agent for about 1-4 weeks, about 1-3 months, about 3-6 months, about 6-9 months, about 9-12 months, about 12-18 months, about 18-24 months, about 2-5 years, about 5-10 years, or longer.

Useful FAS or FASL inhibitors include bicyclol, FLIP; MET12 (HHIYLGAVNYIY (SEQ ID NO: 3), HHIYL- GATNYIY (SEQ ID NO: 4), or $H^{60}$HIYLGATNYIY$^{71}$ (SEQ ID NO: 4)), or a shorter fragment thereof, such as a tetramer having a sequence YLGA (SEQ ID NO: 5), or a fragment having a sequence homology of at least about 10%, at least about 20%, at least about 30%, at least about 40%, at least about 50%, at least about 60%, at least about 70%, at least about 80%, or at least about 90% sequence homology to MET12, including compound having a sequence shown in Table 1 below, such as compound 1, compound 2, compound 3, compound 4, compound 5, compound 6, compound 7, compound 8, compound 9, compound 10, or compound 11, ONL1204 (e.g. a peptide comprising or consisting of a sequence HHIYLGATNYIY (SEQ ID NO: 4)); other MET12 derivatives such as a compound having a sequence: $H^{60}$HIYLGATNYIY$^{71}$-$NH_2$ (SEQ ID NO: 4), FAS apoptotic inhibitory molecule [FAIM]; NOL3 [nucleolar protein 3 (apoptosis repressor with CARD domain [ARC]), etc.]; human decoy receptor 1 (DcR1); human decoy receptor 2 (DcR2); or human decoy receptor 3 (DcR3).

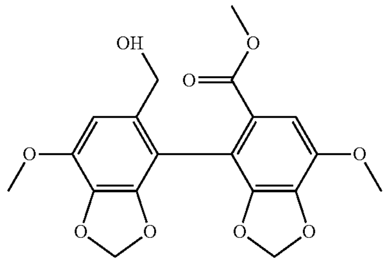

Bicyclol (BC)

TABLE 1

| Compound | Sequence | SEQ ID NO: |
|---|---|---|
| 1 | YLGA | 5 |
| 2 | IYLGA | 6 |
| 3 | YLGAV | 7 |
| 4 | HIYLGA | 8 |
| 5 | IYLGAV | 9 |
| 6 | HIYLGAV | 10 |
| 7 | IYLGAVN | 11 |
| 8 | HHIYLGA | 12 |
| 9 | YLGAVNY | 13 |
| 10 | HHIYLGAV | 14 |
| 11 | YLGAVNYI | 15 |

Any suitable amount of a FAS or FASL inhibitor, such as bicyclol, FLIP, compound 1, compound 2, compound 3, compound 4, compound 5, compound 6, compound 7, compound 8, compound 9, compound 10, or compound 11, ONL1204, $H^{60}$HIYLGATNYIY$^{71}$-$NH_2$ (SEQ ID NO: 4), FAIM, NOL3, DcR1, DcR2, DcR3, etc., may be used in the drug delivery system. For example, a drug delivery system may contain about 0.01-1 μg, about 1-2 μg, about 2-3 μg, about 3-4 μg, about 4-5 μg, about 5-6 μg, about 6-7 μg, about 7-8 μg, about 8-9 μg, about 9-10 μg, about 0.01-3 μg, about 3-6 μg, about 6-10 μg, about 0.01-10 μg, about 10-20 μg, about 20-30 μg, about 30-40 μg, about 40-50 μg, about 50-60 μg, about 60-70 μg, about 70-80 μg, about 80-90 μg, about 90-100 μg, about 0.01-30 μg, about 30-60 μg, about 60-100 μg, about 0.01-100 μg, about 0.1-100 μg, about 100-200 μg, about 200-300 μg, about 300-400 μg, about 400-500 μg, about 500-600 μg, about 600-700 μg, about 700-800 μg, about 800-900 μg, about 900-1,000 μg, about 0.01-300 μg, about 300-600 μg, about 600-1,000 μg, about 0.01-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for a FAS or FASL inhibitor, such as bicyclol, FLIP, compound 1, compound 2, compound 3, compound 4, compound 5, compound 6, compound 7, compound 8, compound 9, compound 10, or compound 11, ONL1204, $H^{60}$HIYLGATNYIY$^{71}$-$NH_2$ (SEQ ID NO: 4), FAIM, NOL3, DcR1, DcR2, DcR3, etc., in a drug delivery system, may provide a drug delivery system that provides therapeutic levels of the FAS or FASL inhibitor for about 1-4 weeks, about 1-3 months, about 3-6 months, about 6-9 months, about 9-12 months, about 12-18 months, about 18-24 months, about 2-5 years, about 5-10 years, or longer.

Useful TNF-α or TNFR inhibitors include etanercept, infliximab, golimumab, certolizumab, adalimumab, TNFR1-selective antagonistic mutant TNF (R1antTNF), DMS5540, TNF Receptor-One Silencer (TROS), ATROSAB.

Any suitable amount of a TNF-α or a TNFR inhibitor, such as etanercept, infliximab, golimumab, certolizumab, adalimumab, R1antTNF, DMS5540, TROS, ATROSAB, etc., may be used in the drug delivery system. For example, a drug delivery system may contain about 0.01-1 μg, about 1-2 μg, about 2-3 μg, about 3-4 μg, about 4-5 μg, about 5-6 μg, about 6-7 μg, about 7-8 μg, about 8-9 μg, about 9-10 μg, about 0.01-3 μg, about 3-6 μg, about 6-10 μg, about 0.01-10 μg, about 10-20 μg, about 20-30 μg, about 30-40 μg, about 40-50 μg, about 50-60 μg, about 60-70 μg, about 70-80 μg, about 80-90 μg, about 90-100 μg, about 0.01-30 μg, about 30-60 μg, about 60-100 μg, about 0.01-100 μg, about 0.1-100 μg, about 100-200 μg, about 200-300 μg, about 300-400 μg, about 400-500 μg, about 500-600 μg, about 600-700 μg, about 700-800 μg, about 800-900 μg, about 900-1,000 μg, about 0.01-300 μg, about 300-600 μg, about 600-1,000 μg, about 0.01-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for a TNF-α or a TNFR inhibitor, such as etanercept, infliximab, golimumab, certolizumab, adalimumab, R1antTNF, DMS5540, TROS, ATROSAB, etc., in a drug delivery system, may provide a drug delivery system that provides therapeutic levels of the TNF-α or the TNFR inhibitor for about 1-4 weeks, about 1-3 months, about 3-6 months, about 6-9 months, about 9-12 months, about 12-18 months, about 18-24 months, about 2-5 years, about 5-10 years, or longer.

Useful mitochondrial peptides include humanin, humanin analogs (e.g. s14G-Humanin, MTP101, elamipretide, etc.)

Any suitable amount of a mitochondrial peptide, such as a humanin, a humanin analogs, s14G-humanin, MTP101, elamipretide, etc., may be used in the drug delivery system. For example, a drug delivery system may contain about 0.01-1 μg, about 1-2 μg, about 2-3 μg, about 3-4 μg, about 4-5 μg, about 5-6 μg, about 6-7 μg, about 7-8 μg, about 8-9 μg, about 9-10 μg, about 0.01-3 μg, about 3-6 μg, about 6-10 μg, about 0.01-10 μg, about 10-20 μg, about 20-30 μg, about 30-40 μg, about 40-50 μg, about 50-60 μg, about 60-70 μg, about 70-80 μg, about 80-90 μg, about 90-100 μg, about 0.01-30 μg, about 30-60 μg, about 60-100 μg, about 0.01-100 μg, about 0.1-100 μg, about 100-200 μg, about 200-300 μg, about 300-400 μg, about 400-500 μg, about 500-600 μg, about 600-700 μg, about 700-800 μg, about 800-900 μg, about 900-1,000 μg, about 0.0100-300 μg, about 300-600 μg, about 600-1,000 μg, about 0.01-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for a mitochondrial peptide, such as a humanin, a humanin analogs, s14G-humanin, MTP101, elamipretide, etc., in a drug delivery system, may provide a drug delivery system that provides therapeutic levels of the mitochondrial peptide for about 1-4 weeks, about 1-3 months, about 3-6 months, about 6-9 months, about 9-12 months, about 12-18 months, about 18-24 months, about 2-5 years, about 5-10 years, or longer.

Useful oligonucleotides include DNA, RNA, etc. In some embodiments, the oligonucleotide is a short inhibitory RNA, or "siRNA." siRNAs can induce the RNA interference (RNAi) pathway. siRNAs can vary in length (generally 20-25 base pairs) and contain varying degrees of complementarity to their target mRNA in the antisense strand. Some, but not all, siRNA have unpaired overhanging bases on the 5' or 3' end of the sense strand and/or the antisense strand. siRNA includes duplexes of two separate strands, as well as single strands that can form hairpin structures comprising a duplex region. In some embodiments, the siRNA is targeting FAS (as FAS-targeting siRNA), such as FAS siRNA sense (5'-GAAACGAACUGCACCCGGAU-3' (SEQ ID NO: 16)); or negative siRNA sense (5'-UAGCGACUAAACACAUCAA-3' (SEQ ID NO: 17)). In some embodiments, the siRNA is TNF-α targeting.

Any suitable amount of an oligonucleotide, such as a DNA, an RNA, siRNA, FAS-targeting siRNA, FAS siRNA sense, negative siRNA sense, TNF-α targeting siRNA, etc., may be used in the drug delivery system. For example, a drug delivery system may contain about 0.01-1 μg, about 1-2 μg, about 2-3 μg, about 3-4 μg, about 4-5 μg, about 5-6 μg, about 6-7 μg, about 7-8 μg, about 8-9 μg, about 9-10 μg, about 0.01-3 μg, about 3-6 μg, about 6-10 μg, about 0.01-10 μg, about 10-20 μg, about 20-30 μg, about 30-40 μg, about 40-50 μg, about 50-60 μg, about 60-70 μg, about 70-80 μg, about 80-90 μg, about 90-100 μg, about 0.01-30 μg, about 30-60 μg, about 60-100 μg, about 0.01-100 μg, about 0.1-100 μg, about 100-200 μg, about 200-300 μg, about 300-400 μg, about 400-500 μg, about 500-600 μg, about 600-700 μg, about 700-800 μg, about 800-900 μg, about 900-1,000 μg, about 0.01-300 μg, about 300-600 μg, about 600-1,000 μg, about 0.01-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for an oligonucleotide, such as a DNA, an RNA, siRNA, FAS-targeting siRNA, FAS siRNA sense, negative siRNA sense, TNF-α targeting siRNA, etc., in a drug delivery system, may provide a drug delivery system that provides therapeutic levels of the oligonucleotide for about 1-4 weeks, about 1-3 months, about 3-6 months, about 6-9 months, about 9-12 months, about 12-18 months, about 18-24 months, about 2-5 years, about 5-10 years, or longer.

Useful chemokine inhibitors include NR58.3-14-3.

NR58.3-14-3

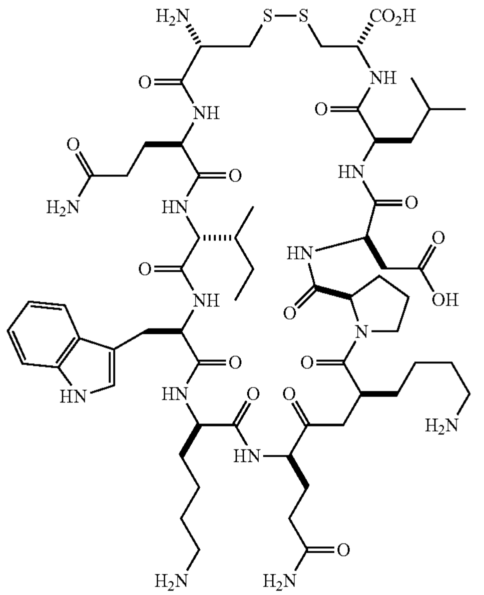

Any suitable amount of a chemokine inhibitor, such as NR58.3-14-3, etc., may be used in the drug delivery system. For example, a drug delivery system may contain about 0.01-1 μg, about 1-2 μg, about 2-3 μg, about 3-4 μg, about 4-5 μg, about 5-6 μg, about 6-7 μg, about 7-8 μg, about 8-9 μg, about 9-10 μg, about 0.01-3 μg, about 3-6 μg, about 6-10 μg, about 0.01-10 μg, about 10-20 μg, about 20-30 μg, about 30-40 μg, about 40-50 μg, about 50-60 μg, about 60-70 μg, about 70-80 μg, about 80-90 μg, about 90-100 μg, about 0.01-30 μg, about 30-60 μg, about 60-100 μg, about 0.01-100 μg, about 0.1-100 μg, about 100-200 μg, about 200-300 μg, about 300-400 μg, about 400-500 μg, about 500-600 μg, about 600-700 μg, about 700-800 μg, about 800-900 μg, about 900-1,000 μg, about 0.01-300 μg, about 300-600 μg, about 600-1,000 μg, about 0.01-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for chemokine inhibitor, such as NR58.3-14-3, etc., in a drug delivery system, may provide a drug delivery system that provides therapeutic levels of the chemokine inhibitor for about 1-4 weeks, about 1-3 months, about 3-6 months, about 6-9 months, about 9-12 months, about 12-18 months, about 18-24 months, about 2-5 years, about 5-10 years, or longer.

Useful cysteine-aspartic proteases (caspase) or caspase inhibitors include a caspase 2 inhibitor, a caspase 3 inhibitor, a caspase 8 inhibitor, a caspase 9 inhibitor, etc.

Any suitable amount of a caspase or a caspase inhibitor, such as a caspase 2 inhibitor, a caspase 3 inhibitor, a caspase 8 inhibitor, a caspase 9 inhibitor, etc., may be used in the drug delivery system. For example, a drug delivery system may contain about 0.01-1 μg, about 1-2 μg, about 2-3 μg, about 3-4 μg, about 4-5 μg, about 5-6 μg, about 6-7 μg, about 7-8 μg, about 8-9 μg, about 9-10 μg, about 0.01-3 μg, about 3-6 μg, about 6-10 μg, about 0.01-10 μg, about 10-20 μg, about 20-30 μg, about 30-40 μg, about 40-50 μg, about 50-60 μg, about 60-70 μg, about 70-80 μg, about 80-90 μg, about 90-100 μg, about 0.01-30 μg, about 30-60 μg, about 60-100 μg, about 0.01-100 μg, about 0.1-100 μg, about 100-200 μg, about 200-300 μg, about 300-400 μg, about 400-500 μg, about 500-600 μg, about 600-700 μg, about 700-800 μg, about 800-900 μg, about 900-1,000 μg, about 0.01-300 μg, about 300-600 μg, about 600-1,000 μg, about 0.01-1 mg, about 1-2 mg, about 2-3 mg, about 3-4 mg, about 4-5 mg, about 5-6 mg, about 6-7 mg, about 7-8 mg, about 8-9 mg, about 9-10 mg, about 0.01-3 mg, about 3-6 mg, about 6-10 mg, or about 0.01-10 mg of one of these compounds. These amounts may also apply to a situation where the drug is present in a covalently bonded form, such as to another drug or to the sustained delivery component.

Use of the amounts given above for a caspase inhibitor, such as a caspase 2 inhibitor, a caspase 3 inhibitor, a caspase 8 inhibitor, a caspase 9 inhibitor, etc., in a drug delivery system, may provide a drug delivery system that provides therapeutic levels of the caspase inhibitor for about 1-4 weeks, about 1-3 months, about 3-6 months, about 6-9 months, about 9-12 months, about 12-18 months, about 18-24 months, about 2-5 years, about 5-10 years, or longer.

A drug delivery system may contain two different compounds that are a neurotrophic agent, a FAS/FASL inhibitor, a TNF-α/TNFR inhibitor, a mitochondrial peptide, an oligonucleotide, a chemokine inhibitor, or a cysteine-aspartic protease (caspase) or a caspase inhibitor. For example, the first compound and the second compound may those identified in Table 2.

TABLE 2

| First Compound | Second Compound |
|---|---|
| a neurotrophic agent | a neurotrophic agent |
| a FAS/FASL inhibitor | a FAS/FASL inhibitor |
| a TNF-α/TNFR inhibitor | a TNF-α/TNFR inhibitor |
| a mitochondrial peptide | a mitochondrial peptide |
| an oligonucleotide | an oligonucleotide |
| a chemokine inhibitor | a chemokine inhibitor |
| a caspase inhibitor | a caspase inhibitor |
| a neurotrophic agent | a FAS/FASL inhibitor |
| a neurotrophic agent | a TNF-α/TNFR inhibitor |
| a neurotrophic agent | a mitochondrial peptide |
| a neurotrophic agent | an oligonucleotide |
| a neurotrophic agent | a chemokine inhibitor |
| a neurotrophic agent | a caspase inhibitor |
| a FAS/FASL inhibitor | a TNF-α/TNFR inhibitor |
| a FAS/FASL inhibitor | a mitochondrial peptide |
| a FAS/FASL inhibitor | an oligonucleotide |
| a FAS/FASL inhibitor | a chemokine inhibitor |
| a FAS/FASL inhibitor | a caspase inhibitor |
| a TNF-α/TNFR inhibitor | a mitochondrial peptide |
| a TNF-α/TNFR inhibitor | an oligonucleotide |
| a TNF-α/TNFR inhibitor | a chemokine inhibitor |
| a TNF-α/TNFR inhibitor | a caspase inhibitor |

TABLE 2-continued

| First Compound | Second Compound |
|---|---|
| an oligonucleotide | a chemokine inhibitor |
| an oligonucleotide | a caspase inhibitor |
| a chemokine inhibitor | a caspase inhibitor |

With respect two each combination identified in Table 2, in some embodiments, the First Compound and the Second Compound are covalently bound to one another. In some embodiments, the First Compound and the Second Compound are covalently bound to one another via a linking group.

For example, some combinations bound by a linking group are represented in Formula 1, I, 2, A, B, D, E, F, G, H, J, K, M, N, O, P, Q, R, S, T, and U:

| | | | |
|---|---|---|---|
| Neu-L-FAS<br>Formula 1 | Neu-L-TNF<br>Formula I | Neu-L-Mit<br>Formula 2 | Nuc-L-FAS<br>Formula A |
| Nuc-L-TNF<br>Formula B | Nuc-L-Neu<br>Formula D | Neu-L-CK<br>Formula E | Neu-L-CAS<br>Formula F |
| FAS-L-TNF<br>Formula G | FAS-L-Mit<br>Formula H | FAS-L-CK<br>Formula J | FAS-L-CAS<br>Formula K |
| TNF-L-Mit<br>Formula M | TNF-L-CK<br>Formula N | TNF-L-CAS<br>Formula O | Mit-L-Nuc<br>Formula P |
| Mit-L-CK<br>Formula Q | Mit-L-CAS<br>Formula R | Nuc-L-CK<br>Formula S | Nuc-L-CAS<br>Formula T |
| | CK-L-CAS<br>Formula U | | |

In some embodiments, a drug delivery system comprises one of the following drug combinations, including salts, free acids, or free bases of the drugs, either covalently linked (such as by a linking group L, including groups represented by Formula L-1, L-2, L-3, L-4, L-5, L-6, L-7, or L-8) or not covalently linked: CNTF and a protein derivative of CNTF; CNTF and a CNTF peptide; CNTF and Peptide 21; CNTF and Peptide 21; CNTF and rhCNTF; CNTF and NGF; CNTF and BDNF; CNTF and GDNF; CNTF and bicyclol; CNTF and FLIP; CNTF and MET12; CNTF and compound 1 from Table 1; CNTF and compound 2 from Table 1; CNTF and compound 3 from Table 1; CNTF and compound 4 from Table 1; CNTF and compound 5 from Table 1; CNTF and compound 6 from Table 1; CNTF and compound 7 from Table 1; CNTF and compound 8 from Table 1; CNTF and compound 9 from Table 1; CNTF and compound 10 from Table 1; CNTF and or compound 11 from Table 1; CNTF and ONL1204; CNTF and $H^{60}HIYLGATNYIY^{71}-NH_2$ (SEQ ID NO: 4); CNTF and FAIM; CNTF and NOL3; CNTF and DcR1; CNTF and DcR2; CNTF and DcR3; CNTF and etanercept; CNTF and infliximab; CNTF and golimumab; CNTF and certolizumab; CNTF and adalimumab; CNTF and R1antTNF; CNTF and DMS5540; CNTF and TROS; CNTF and ATROSAB; CNTF and humanin; CNTF and a humanin analog; CNTF and s14G-humanin; CNTF and MTP101; CNTF and elamipretide; CNTF and DNA; CNTF and RNA; CNTF and a siRNA; CNTF and FAS-targeting siRNA; CNTF and FAS siRNA sense; CNTF and negative siRNA sense; CNTF and TNF-α targeting siRNA; CNTF and NR58.3-14-3; CNTF and a caspase 2 inhibitor; CNTF and a caspase 3 inhibitor; CNTF and a caspase 8 inhibitor; CNTF and a caspase 9 inhibitor; a protein derivative of CNTF and a CNTF peptide; a protein derivative of CNTF and Peptide 21; a protein derivative of CNTF and Peptide 21; a protein derivative of CNTF and rhCNTF; a protein derivative of CNTF and NGF; a protein derivative of CNTF and BDNF; a protein derivative of CNTF and GDNF; a protein derivative of CNTF and bicyclol; a protein derivative of CNTF and FLIP; a protein derivative of CNTF and MET12; a protein derivative of CNTF and compound 1 from Table 1; a protein derivative of CNTF and compound 2 from Table 1; a protein derivative of CNTF and compound 3 from Table 1; a protein derivative of CNTF and compound 4 from Table 1; a protein derivative of CNTF and compound 5 from Table 1; a protein derivative of CNTF and compound 6 from Table 1; a protein derivative of CNTF and compound 7 from Table 1; a protein derivative of CNTF and compound 8 from Table 1; a protein derivative of CNTF and compound 9 from Table 1; a protein derivative of CNTF and compound 10 from Table 1; a protein derivative of CNTF and or compound 11 from Table 1; a protein derivative of CNTF and ONL1204; a protein derivative of CNTF and $H^{60}HIYLGATNYIY^{71}-NH_2$ (SEQ ID NO: 4); a protein derivative of CNTF and FAIM; a protein derivative of CNTF and NOL3; a protein derivative of CNTF and DcR1; a protein derivative of CNTF and DcR2; a protein derivative of CNTF and DcR3; a protein derivative of CNTF and etanercept; a protein derivative of CNTF and infliximab; a protein derivative of CNTF and golimumab; a protein derivative of CNTF and certolizumab; a protein derivative of CNTF and adalimumab; a protein derivative of CNTF and R1antTNF; a protein derivative of CNTF and DMS5540; a protein derivative of CNTF and TROS; a protein derivative of CNTF and ATROSAB; a protein derivative of CNTF and humanin; a protein derivative of CNTF and a humanin analog; a protein derivative of CNTF and s14G-humanin; a protein derivative of CNTF and MTP101; a protein derivative of CNTF and elamipretide; a protein derivative of CNTF and DNA; a protein derivative of CNTF and RNA; a protein derivative of CNTF and a siRNA; a protein derivative of CNTF and FAS-targeting siRNA; a protein derivative of CNTF and FAS siRNA sense; a protein derivative of CNTF and negative siRNA sense; a protein derivative of CNTF and TNF-α targeting siRNA; a protein derivative of CNTF and NR58.3-14-3; a protein derivative of CNTF and a caspase 2 inhibitor; a protein derivative of CNTF and a caspase 3 inhibitor; a protein derivative of CNTF and a caspase 8 inhibitor; a protein derivative of CNTF and a caspase 9 inhibitor; a CNTF peptide and Peptide 21; a CNTF peptide and rhCNTF; a CNTF peptide and NGF; a CNTF peptide and BDNF; a CNTF peptide and GDNF; a CNTF peptide and bicyclol; a CNTF peptide and FLIP; a CNTF peptide and MET12; a CNTF peptide and compound 1 from Table 1; a CNTF peptide and compound 2 from Table 1; a CNTF peptide and compound 3 from Table 1; a CNTF peptide and compound 4 from Table 1; a CNTF peptide and compound 5 from Table 1; a CNTF peptide and compound 6 from Table 1; a CNTF peptide and compound 7 from Table 1; a CNTF peptide and compound 8 from Table 1; a CNTF peptide and compound 9 from Table 1; a CNTF peptide and compound 10 from Table 1; a CNTF peptide and or compound 11 from Table 1; a CNTF peptide and ONL1204; a CNTF peptide and $H^{60}HIYLGATNYIY^{71}-NH_2$ (SEQ ID NO: 4); a CNTF peptide and FAIM; a CNTF peptide and NOL3; a CNTF peptide and DcR1; a CNTF peptide and DcR2; a CNTF peptide and DcR3; a CNTF peptide and etanercept; a CNTF peptide and infliximab; a CNTF peptide and golimumab; a CNTF peptide and certolizumab; a CNTF peptide and adalimumab; a CNTF peptide and R1antTNF; a CNTF peptide and DMS5540; a CNTF peptide and TROS; a CNTF peptide and ATROSAB; a CNTF peptide and humanin; a CNTF peptide and a humanin analog; a CNTF peptide and s14G-humanin; a CNTF peptide and MTP101; a CNTF peptide and elamipretide; a CNTF peptide and DNA; a CNTF peptide and RNA; a CNTF peptide and a siRNA; a CNTF peptide and FAS-targeting siRNA; a CNTF peptide and FAS siRNA sense; a CNTF peptide and negative siRNA sense; a CNTF peptide and TNF-α targeting siRNA; a CNTF peptide and NR58.3-14-3; a CNTF peptide and a caspase 2 inhibitor; a CNTF peptide and a caspase 3 inhibitor; a CNTF peptide and a caspase 8 inhibitor; a CNTF peptide and a caspase 9 inhibitor; Peptide 21 and rhCNTF; Peptide 21 and NGF; Peptide 21 and BDNF; Peptide 21 and GDNF; Peptide 21 and bicyclol; Peptide 21 and FLIP; Peptide 21 and MET12; Peptide 21 and compound 1 from Table 1; Peptide 21 and compound 2 from Table 1; Peptide 21 and compound 3 from Table 1; Peptide 21 and compound 4 from Table 1; Peptide 21 and compound 5 from Table 1; Peptide 21 and compound 6 from Table 1; Peptide 21 and compound 7 from Table 1; Peptide 21 and compound 8 from Table 1; Peptide 21 and compound 9 from Table 1; Peptide 21 and compound 10 from Table 1; Peptide 21 and or compound 11 from Table 1; Peptide 21 and ONL1204; Peptide 21 and $H^{60}HIYLGATNYIY^{71}-NH_2$ (SEQ ID NO: 4); Peptide 21 and FAIM; Peptide 21 and NOL3; Peptide 21 and DcR1; Peptide 21 and DcR2; Peptide 21 and DcR3; Peptide 21 and etanercept; Peptide 21 and infliximab; Peptide 21 and golimumab; Peptide 21 and certolizumab; Peptide 21 and adalimumab; Peptide 21 and R1antTNF; Peptide 21 and DMS5540; Peptide 21 and TROS; Peptide 21 and ATROSAB; Peptide 21 and humanin; Peptide 21 and a humanin analog; Peptide 21 and s14G-humanin; Peptide 21 and MTP101; Peptide 21 and elamipretide; Peptide 21 and DNA; Peptide 21 and RNA; Peptide 21 and a siRNA; Peptide 21 and FAS-targeting siRNA; Peptide 21 and FAS siRNA sense; Peptide 21 and negative siRNA sense; Peptide 21 and TNF-α targeting siRNA; Peptide 21 and NR58.3-14-3; Peptide 21 and a caspase 2 inhibitor; Peptide 21 and a caspase 3; Peptide 21 and a caspase 8 inhibitor; Peptide 21 and a caspase 9 inhibitor; rhCNTF and NGF; rhCNTF and BDNF; rhCNTF and GDNF; rhCNTF and bicyclol; rhCNTF and FLIP; rhCNTF and MET12; rhCNTF and compound 1 from Table 1; rhCNTF and compound 2 from Table 1; rhCNTF and compound 3 from Table 1; rhCNTF and compound 4 from Table 1; rhCNTF and compound 5 from Table 1; rhCNTF and compound 6 from Table 1; rhCNTF and compound 7 from Table 1; rhCNTF and compound 8 from Table 1; rhCNTF and compound 9 from Table 1; rhCNTF and compound 10 from Table 1; rhCNTF and or compound 11 from Table 1; rhCNTF and ONL1204; rhCNTF and $H^{60}HIYLGATNYIY^{71}-NH_2$ (SEQ ID NO: 4); rhCNTF and FAIM; rhCNTF and NOL3; rhCNTF and DcR1; rhCNTF and DcR2; rhCNTF and DcR3; rhCNTF and etanercept; rhCNTF and infliximab; rhCNTF and golimumab; rhCNTF and certolizumab; rhCNTF and adalimumab; rhCNTF and R1antTNF; rhCNTF and DMS5540; rhCNTF and TROS; rhCNTF and ATROSAB; rhCNTF and humanin; rhCNTF and a humanin analog; rhCNTF and s14G-humanin; rhCNTF and MTP101; rhCNTF and elamipretide; rhCNTF and DNA; rhCNTF and RNA; rhCNTF and a siRNA; rhCNTF and FAS-targeting siRNA; rhCNTF and FAS siRNA sense; rhCNTF and negative siRNA sense; rhCNTF and TNF-α targeting siRNA; rhCNTF and NR58.3-14-3; rhCNTF and a caspase 2 inhibitor; rhCNTF and a caspase 3 inhibitor; rhCNTF and a caspase 8 inhibitor; rhCNTF and a caspase 9 inhibitor; NGF and BDNF; NGF and GDNF; NGF and bicyclol; NGF and FLIP; NGF and MET12; NGF and compound 1 from Table 1; NGF and compound 2 from Table 1; NGF and compound 3 from Table 1; NGF and compound 4 from Table 1; NGF and compound 5 from Table 1; NGF and compound 6 from Table 1; NGF and compound 7 from Table 1; NGF and compound 8 from Table 1; NGF and compound 9 from Table 1; NGF and compound 10 from Table 1; NGF and or compound 11 from Table 1; NGF and ONL1204; NGF and $H^{60}$HIYLGATNYIY$^{71}$-$NH_2$ (SEQ ID NO: 4); NGF and FAIM; NGF and NOL3; NGF and DcR1; NGF and DcR2; NGF and DcR3; NGF and etanercept; NGF and infliximab; NGF and golimumab; NGF and certolizumab; NGF and adalimumab; NGF and R1antTNF; NGF and DMS5540; NGF and TROS; NGF and ATROSAB; NGF and humanin; NGF and a humanin analog; NGF and s14G-humanin; NGF and MTP101; NGF and elamipretide; NGF and DNA; NGF and RNA; NGF and a siRNA; NGF and FAS-targeting siRNA; NGF and FAS siRNA sense; NGF and negative siRNA sense; NGF and TNF-α targeting siRNA; NGF and NR58.3-14-3; NGF and a caspase 2 inhibitor; NGF and a caspase 3 inhibitor; NGF and a caspase 8 inhibitor; NGF and a caspase 9 inhibitor; BDNF and GDNF; BDNF and bicyclol; BDNF and FLIP; BDNF and MET12; BDNF and compound 1 from Table 1; BDNF and compound 2 from Table 1; BDNF and compound 3 from Table 1; BDNF and compound 4 from Table 1; BDNF and compound 5 from Table 1; BDNF and compound 6 from Table 1; BDNF and compound 7 from Table 1; BDNF and compound 8 from Table 1; BDNF and compound 9 from Table 1; BDNF and compound 10 from Table 1; BDNF and or compound 11 from Table 1; BDNF and ONL1204; BDNF and $H^{60}$HIYLGATNYIY$^{71}$-$NH_2$ (SEQ ID NO: 4); BDNF and FAIM; BDNF and NOL3; BDNF and DcR1; BDNF and DcR2; BDNF and DcR3; BDNF and etanercept; BDNF and infliximab; BDNF and golimumab; BDNF and certolizumab; BDNF and adalimumab; BDNF and R1antTNF; BDNF and DMS5540; BDNF and TROS; BDNF and ATROSAB; BDNF and humanin; BDNF and a humanin analog; BDNF and s14G-humanin; BDNF and MTP101; BDNF and elamipretide; BDNF and DNA; BDNF and RNA; BDNF and a siRNA; BDNF and FAS-targeting siRNA; BDNF and FAS siRNA sense; BDNF and negative siRNA sense; BDNF and TNF-α targeting siRNA; BDNF and NR58.3-14-3; BDNF and a caspase 2 inhibitor; BDNF and a caspase 3 inhibitor; BDNF and a caspase 8 inhibitor; BDNF and a caspase 9 inhibitor; GDNF and bicyclol; GDNF and FLIP; GDNF and MET12; GDNF and compound 1 from Table 1; GDNF and compound 2 from Table 1; GDNF and compound 3 from Table 1; GDNF and compound 4 from Table 1; GDNF and compound 5 from Table 1; GDNF and compound 6 from Table 1; GDNF and compound 7 from Table 1; GDNF and compound 8 from Table 1; GDNF and compound 9 from Table 1; GDNF and compound 10 from Table 1; GDNF and or compound 11 from Table 1; GDNF and ONL1204; GDNF and $H^{60}$HIYLGATNYIY$^{71}$—$NH_2$ (SEQ ID NO: 4); GDNF and FAIM; GDNF and NOL3; GDNF and DcR1; GDNF and DcR2; GDNF and DcR3; GDNF and etanercept; GDNF and infliximab; GDNF and golimumab; GDNF and certolizumab; GDNF and adalimumab; GDNF and R1antTNF; GDNF and DMS5540; GDNF and TROS; GDNF and ATROSAB; GDNF and humanin; GDNF and a humanin analog; GDNF and s14G-humanin; GDNF and MTP101; GDNF and elamipretide; GDNF and DNA; GDNF and RNA; GDNF and a siRNA; GDNF and FAS-targeting siRNA; GDNF and FAS siRNA sense; GDNF and negative siRNA sense; GDNF and TNF-α targeting siRNA; GDNF and NR58.3-14-3; GDNF and a caspase 2 inhibitor; GDNF and a caspase 3 inhibitor; GDNF and a caspase 8 inhibitor; GDNF and a caspase 9 inhibitor; bicyclol and FLIP; bicyclol and MET12; bicyclol and compound 1 from Table 1; bicyclol and compound 2 from Table 1; bicyclol and compound 3 from Table 1; bicyclol and compound 4 from Table 1; bicyclol and compound 5 from Table 1; bicyclol and compound 6 from Table 1; bicyclol and compound 7 from Table 1; bicyclol and compound 8 from Table 1; bicyclol and compound 9 from Table 1; bicyclol and compound 10 from Table 1; bicyclol and or compound 11 from Table 1; bicyclol and ONL1204; bicyclol and $H^{60}$HIYLGATNYIY$^{71}$—$NH_2$ (SEQ ID NO: 4); bicyclol and FAIM; bicyclol and NOL3; bicyclol and DcR1; bicyclol and DcR2; bicyclol and DcR3; bicyclol and etanercept; bicyclol and infliximab; bicyclol and golimumab; bicyclol and certolizumab; bicyclol and adalimumab; bicyclol and R1antTNF; bicyclol and DMS5540; bicyclol and TROS; bicyclol and ATROSAB; bicyclol and humanin; bicyclol and a humanin analog; bicyclol and s14G-humanin; bicyclol and MTP101; bicyclol and elamipretide; bicyclol and DNA; bicyclol and RNA; bicyclol and a siRNA; bicyclol and FAS-targeting siRNA; bicyclol and FAS siRNA sense; bicyclol and negative siRNA sense; bicyclol and TNF-α targeting siRNA; bicyclol and NR58.3-14-3; bicyclol and a caspase 2 inhibitor; bicyclol and a caspase 3 inhibitor; bicyclol and a caspase 8 inhibitor; bicyclol and a caspase 9 inhibitor; FLIP and MET12; FLIP and compound 1 from Table 1; FLIP and compound 2 from Table 1; FLIP and compound 3 from Table 1; FLIP and compound 4 from Table 1; FLIP and compound 5 from Table 1; FLIP and compound 6 from Table 1; FLIP and compound 7 from Table 1; FLIP and compound 8 from Table 1; FLIP and compound 9 from Table 1; FLIP and compound 10 from Table 1; FLIP and or compound 11 from Table 1; FLIP and ONL1204; FLIP and $H^{60}$HIYLGATNYIY$^{71}$-$NH_2$ (SEQ ID NO: 4); FLIP and FAIM; FLIP and NOL3; FLIP and DcR1; FLIP and DcR2; FLIP and DcR3; FLIP and etanercept; FLIP and infliximab; FLIP and golimumab; FLIP and certolizumab; FLIP and adalimumab; FLIP and R1antTNF; FLIP and DMS5540; FLIP and TROS; FLIP and ATROSAB; FLIP and humanin; FLIP and a humanin analog; FLIP and s14G-humanin; FLIP and MTP101; FLIP and elamipretide; FLIP and DNA; FLIP and RNA; FLIP and a siRNA; FLIP and FAS-targeting siRNA; FLIP and FAS siRNA sense; FLIP and negative siRNA sense; FLIP and TNF-α targeting siRNA; FLIP and NR58.3-14-3; FLIP and a caspase 2 inhibitor; FLIP and a caspase 3 inhibitor; FLIP and a caspase 8 inhibitor; FLIP and a caspase 9 inhibitor; MET12 and compound 1 from Table 1; MET12 and compound 2 from Table 1; MET12 and compound 3 from Table 1; MET12 and compound 4 from Table 1; MET12 and compound 5 from Table 1; MET12 and compound 6 from Table 1; MET12 and compound 7 from Table 1; MET12 and compound 8 from Table 1; MET12 and compound 9 from Table 1; MET12 and compound 10 from Table 1; MET12 and or compound 11 from Table 1; MET12 and ONL1204; MET12 and $H^{60}$HIYLGATNYIY$^{71}$-$NH_2$ (SEQ ID NO: 4); MET12 and FAIM; MET12 and NOL3; MET12 and DcR1; MET12 and DcR2; MET12 and DcR3; MET12 and etanercept; MET12 and infliximab; MET12 and golimumab; MET12 and certolizumab; MET12 and adalimumab; MET12 and R1antTNF; MET12 and DMS5540; MET12 and TROS; MET12 and ATROSAB; MET12 and humanin; MET12 and a humanin analog; MET12 and s14G-humanin; MET12 and MTP101; MET12 and elamipretide; MET12 and DNA; MET12 and RNA; MET12 and a siRNA; MET12 and FAS-targeting siRNA; MET12 and FAS siRNA sense; MET12 and negative siRNA sense; MET12 and TNF-α targeting siRNA; MET12 and NR58.3-14-3; MET12 and a caspase 2 inhibitor; MET12 and a caspase 3 inhibitor; MET12 and a caspase 8 inhibitor; MET12 and a caspase 9 inhibitor; compound 1 from Table 1 and compound 2 from Table 1; compound 1 from Table 1 and compound 3 from Table 1; compound 1 from Table 1 and compound 4 from Table 1; compound 1 from Table 1 and compound 5 from Table 1; compound 1 from Table 1 and compound 6 from Table 1; compound 1 from Table 1 and compound 7 from Table 1; compound 1 from Table 1 and compound 8 from Table 1; compound 1 from Table 1 and compound 9 from Table 1; compound 1 from Table 1 and compound 10 from Table 1; compound 1 from Table 1 and or compound 11 from Table 1; compound 1 from Table 1 and ONL1204; compound 1 from Table 1 and $H^{60}HIYLGATNYIY^{71}-NH_2$ (SEQ ID NO: 4); compound 1 from Table 1 and FAIM; compound 1 from Table 1 and NOL3; compound 1 from Table 1 and DcR1; compound 1 from Table 1 and DcR2; compound 1 from Table 1 and DcR3; compound 1 from Table 1 and etanercept; compound 1 from Table 1 and infliximab; compound 1 from Table 1 and golimumab; compound 1 from Table 1 and certolizumab; compound 1 from Table 1 and adalimumab; compound 1 from Table 1 and R1antTNF; compound 1 from Table 1 and DMS5540; compound 1 from Table 1 and TROS; compound 1 from Table 1 and ATROSAB; compound 1 from Table 1 and humanin; compound 1 from Table 1 and a humanin analog; compound 1 from Table 1 and s14G-humanin; compound 1 from Table 1 and MTP101; compound 1 from Table 1 and elamipretide; compound 1 from Table 1 and DNA; compound 1 from Table 1 and RNA; compound 1 from Table 1 and a siRNA; compound 1 from Table 1 and FAS-targeting siRNA; compound 1 from Table 1 and FAS siRNA sense; compound 1 from Table 1 and negative siRNA sense; compound 1 from Table 1 and TNF-α targeting siRNA; compound 1 from Table 1 and NR58.3-14-3; compound 1 from Table 1 and a caspase 2 inhibitor; compound 1 from Table 1 and a caspase 3 inhibitor; compound 1 from Table 1 and a caspase 8 inhibitor; compound 1 from Table 1 and a caspase 9 inhibitor; compound 2 from Table 1 and compound 3 from Table 1; compound 2 from Table 1 and compound 4 from Table 1; compound 2 from Table 1 and compound 5 from Table 1; compound 2 from Table 1 and compound 6 from Table 1; compound 2 from Table 1 and compound 7 from Table 1; compound 2 from Table 1 and compound 8 from Table 1; compound 2 from Table 1 and compound 9 from Table 1; compound 2 from Table 1 and compound 10 from Table 1; compound 2 from Table 1 and or compound 11 from Table 1; compound 2 from Table 1 and ONL1204; compound 2 from Table 1 and $H^{60}HIYLGATNYIY^{71}-NH_2$ (SEQ ID NO: 4); compound 2 from Table 1 and FAIM; compound 2 from Table 1 and NOL3; compound 2 from Table 1 and DcR1; compound 2 from Table 1 and DcR2; compound 2 from Table 1 and DcR3; compound 2 from Table 1 and etanercept; compound 2 from Table 1 and infliximab; compound 2 from Table 1 and golimumab; compound 2 from Table 1 and certolizumab; compound 2 from Table 1 and adalimumab; compound 2 from Table 1 and R1antTNF; compound 2 from Table 1 and DMS5540; compound 2 from Table 1 and TROS; compound 2 from Table 1 and ATROSAB; compound 2 from Table 1 and humanin; compound 2 from Table 1 and a humanin analog; compound 2 from Table 1 and s14G-humanin; compound 2 from Table 1 and MTP101; compound 2 from Table 1 and elamipretide; compound 2 from Table 1 and DNA; compound 2 from Table 1 and RNA; compound 2 from Table 1 and a siRNA; compound 2 from Table 1 and FAS-targeting siRNA; compound 2 from Table 1 and FAS siRNA sense; compound 2 from Table 1 and negative siRNA sense; compound 2 from Table 1 and TNF-α targeting siRNA; compound 2 from Table 1 and NR58.3-14-3; compound 2 from Table 1 and a caspase 2 inhibitor; compound 2 from Table 1 and a caspase 3 inhibitor; compound 2 from Table 1 and a caspase 8 inhibitor; compound 2 from Table 1 and a caspase 9 inhibitor; compound 3 from Table 1 and compound 4 from Table 1; compound 3 from Table 1 and compound 5 from Table 1; compound 3 from Table 1 and compound 6 from Table 1; compound 3 from Table 1 and compound 7 from Table 1; compound 3 from Table 1 and compound 8 from Table 1; compound 3 from Table 1 and compound 9 from Table 1; compound 3 from Table 1 and compound 10 from Table 1; compound 3 from Table 1 and or compound 11 from Table 1; compound 3 from Table 1 and ONL1204; compound 3 from Table 1 and $H^{60}HIYLGATNYIY^{71}-NH_2$ (SEQ ID NO: 4); compound 3 from Table 1 and FAIM; compound 3 from Table 1 and NOL3; compound 3 from Table 1 and DcR1; compound 3 from Table 1 and DcR2; compound 3 from Table 1 and DcR3; compound 3 from Table 1 and etanercept; compound 3 from Table 1 and infliximab; compound 3 from Table 1 and golimumab; compound 3 from Table 1 and certolizumab; compound 3 from Table 1 and adalimumab; compound 3 from Table 1 and R1antTNF; compound 3 from Table 1 and DMS5540; compound 3 from Table 1 and TROS; compound 3 from Table 1 and ATROSAB; compound 3 from Table 1 and humanin; compound 3 from Table 1 and a humanin analog; compound 3 from Table 1 and s14G-humanin; compound 3 from Table 1 and MTP101; compound 3 from Table 1 and elamipretide; compound 3 from Table 1 and DNA; compound 3 from Table 1 and RNA; compound 3 from Table 1 and a siRNA; compound 3 from Table 1 and FAS-targeting siRNA; compound 3 from Table 1 and FAS siRNA sense; compound 3 from Table 1 and negative siRNA sense; compound 3 from Table 1 and TNF-α targeting siRNA; compound 3 from Table 1 and NR58.3-14-3; compound 3 from Table 1 and a caspase 2 inhibitor; compound 3 from Table 1 and a caspase 3 inhibitor; compound 3 from Table 1 and a caspase 8 inhibitor; compound 3 from Table 1 and a caspase 9 inhibitor; compound 4 from Table 1 and compound 5 from Table 1; compound 4 from Table 1 and compound 6 from Table 1; compound 4 from Table 1 and compound 7 from Table 1; compound 4 from Table 1 and compound 8 from Table 1; compound 4 from Table 1 and compound 9 from Table 1; compound 4 from Table 1 and compound 10 from Table 1; compound 4 from Table 1 and or compound 11 from Table 1; compound 4 from Table 1 and ONL1204; compound 4 from Table 1 and $H^{60}HIYLGATNYIY^{71}-NH_2$ (SEQ ID NO: 4); compound 4 from Table 1 and FAIM; compound 4 from Table 1 and NOL3; compound 4 from Table 1 and DcR1; compound 4 from Table 1 and DcR2; compound 4 from Table 1 and DcR3; compound 4 from Table 1 and etanercept; compound 4 from Table 1 and infliximab; compound 4 from Table 1 and golimumab; compound 4 from Table 1 and certolizumab; compound 4 from Table 1 and adalimumab; compound 4 from Table 1 and R1antTNF; compound 4 from Table 1 and DMS5540; compound 4 from Table 1 and TROS; compound 4 from Table 1 and ATROSAB; compound 4 from Table 1 and humanin; compound 4 from Table 1 and a humanin analog; compound 4 from Table 1 and s14G-humanin; compound 4 from Table 1 and MTP101; compound 4 from Table 1 and elamipretide; compound 4 from Table 1 and DNA; compound 4 from Table 1 and RNA; compound 4 from Table 1 and a siRNA; compound 4 from Table 1 and FAS-targeting siRNA; compound 4 from Table 1 and FAS siRNA sense; compound 4 from Table 1 and negative siRNA sense; compound 4 from Table 1 and TNF-α targeting siRNA; compound 4 from Table 1 and NR58.3-14-3; compound 4 from Table 1 and a caspase 2 inhibitor; compound 4 from Table 1 and a caspase 3 inhibitor; compound 4 from Table 1 and a caspase 8 inhibitor; compound 4 from Table 1 and a caspase 9 inhibitor; compound 5 from Table 1 and compound 6 from Table 1; compound 5 from Table 1 and compound 7 from Table 1; compound 5 from Table 1 and compound 8 from Table 1; compound 5 from Table 1 and compound 9 from Table 1; compound 5 from Table 1 and compound 10 from Table 1; compound 5 from Table 1 and or compound 11 from Table 1; compound 5 from Table 1 and ONL1204; compound 5 from Table 1 and $H^{60}HIYLGATNYIY^{71}-NH_2$ (SEQ ID NO: 4); compound 5 from Table 1 and FAIM; compound 5 from Table 1 and NOL3; compound 5 from Table 1 and DcR1; compound 5 from Table 1 and DcR2; compound 5 from Table 1 and DcR3; compound 5 from Table 1 and etanercept; compound 5 from Table 1 and infliximab; compound 5 from Table 1 and golimumab; compound 5 from Table 1 and certolizumab; compound 5 from Table 1 and adalimumab; compound 5 from Table 1 and R1antTNF; compound 5 from Table 1 and DMS5540; compound 5 from Table 1 and TROS; compound 5 from Table 1 and ATROSAB; compound 5 from Table 1 and humanin; compound 5 from Table 1 and a humanin analog; compound 5 from Table 1 and s14G-humanin; compound 5 from Table 1 and MTP101; compound 5 from Table 1 and elamipretide; compound 5 from Table 1 and DNA; compound 5 from Table 1 and RNA; compound 5 from Table 1 and a siRNA; compound 5 from Table 1 and FAS-targeting siRNA; compound 5 from Table 1 and FAS siRNA sense; compound 5 from Table 1 and negative siRNA sense; compound 5 from Table 1 and TNF-α targeting siRNA; compound 5 from Table 1 and NR58.3-14-3; compound 5 from Table 1 and a caspase 2 inhibitor; compound 5 from Table 1 and a caspase 3 inhibitor; compound 5 from Table 1 and a caspase 8 inhibitor; compound 5 from Table 1 and a caspase 9 inhibitor; compound 6 from Table 1 and compound 7 from Table 1; compound 6 from Table 1 and compound 8 from Table 1; compound 6 from Table 1 and compound 9 from Table 1; compound 6 from Table 1 and compound 10 from Table 1; compound 6 from Table 1 and or compound 11 from Table 1; compound 6 from Table 1 and ONL1204; compound 6 from Table 1 and $H^{60}HIYLGATNYIY^{71}-NH_2$ (SEQ ID NO: 4); compound 6 from Table 1 and FAIM; compound 6 from Table 1 and NOL3; compound 6 from Table 1 and DcR1; compound 6 from Table 1 and DcR2; compound 6 from Table 1 and DcR3; compound 6 from Table 1 and etanercept; compound 6 from Table 1 and infliximab; compound 6 from Table 1 and golimumab; compound 6 from Table 1 and certolizumab; compound 6 from Table 1 and adalimumab; compound 6 from Table 1 and R1antTNF; compound 6 from Table 1 and DMS5540; compound 6 from Table 1 and TROS; compound 6 from Table 1 and ATROSAB; compound 6 from Table 1 and humanin; compound 6 from Table 1 and a humanin analog; compound 6 from Table 1 and s14G-humanin; compound 6 from Table 1 and MTP101; compound 6 from Table 1 and elamipretide; compound 6 from Table 1 and DNA; compound 6 from Table 1 and RNA; compound 6 from Table 1 and a siRNA; compound 6 from Table 1 and FAS-targeting siRNA; compound 6 from Table 1 and FAS siRNA sense; compound 6 from Table 1 and negative siRNA sense; compound 6 from Table 1 and TNF-α targeting siRNA; compound 6 from Table 1 and NR58.3-14-3; compound 6 from Table 1 and a caspase 2 inhibitor; compound 6 from Table 1 and a caspase 3 inhibitor; compound 6 from Table 1 and a caspase 8 inhibitor; compound 6 from Table 1 and a caspase 9 inhibitor; compound 7 from Table 1 and compound 8 from Table 1; compound 7 from Table 1 and compound 9 from Table 1; compound 7 from Table 1 and compound 10 from Table 1; compound 7 from Table 1 and or compound 11 from Table 1; compound 7 from Table 1 and ONL1204; compound 7 from Table 1 and $H^{60}HIYLGATNYIY^{71}-NH_2$ (SEQ ID NO: 4); compound 7 from Table 1 and FAIM; compound 7 from Table 1 and NOL3; compound 7 from Table 1 and DcR1; compound 7 from Table 1 and DcR2; compound 7 from Table 1 and DcR3; compound 7 from Table 1 and etanercept; compound 7 from Table 1 and infliximab; compound 7 from Table 1 and golimumab; compound 7 from Table 1 and certolizumab; compound 7 from Table 1 and adalimumab; compound 7 from Table 1 and R1antTNF; compound 7 from Table 1 and DMS5540; compound 7 from Table 1 and TROS; compound 7 from Table 1 and ATROSAB; compound 7 from Table 1 and humanin; compound 7 from Table 1 and a humanin analog; compound 7 from Table 1 and s14G-humanin; compound 7 from Table 1 and MTP101; compound 7 from Table 1 and elamipretide; compound 7 from Table 1 and DNA; compound 7 from Table 1 and RNA; compound 7 from Table 1 and a siRNA; compound 7 from Table 1 and FAS-targeting siRNA; compound 7 from Table 1 and FAS siRNA sense; compound 7 from Table 1 and negative siRNA sense; compound 7 from Table 1 and TNF-α targeting siRNA; compound 7 from Table 1 and NR58.3-14-3; compound 7 from Table 1 and a caspase 2 inhibitor; compound 7 from Table 1 and a caspase 3 inhibitor; compound 7 from Table 1 and a caspase 8 inhibitor; compound 7 from Table 1 and a caspase 9 inhibitor; compound 8 from Table 1 and compound 9 from Table 1; compound 8 from Table 1 and compound 10 from Table 1; compound 8 from Table 1 and or compound 11 from Table 1; compound 8 from Table 1 and ONL1204; compound 8 from Table 1 and $H^{60}HIYLGATNYIY^{71}-NH_2$ (SEQ ID NO: 4); compound 8 from Table 1 and FAIM; compound 8 from Table 1 and NOL3; compound 8 from Table 1 and DcR1; compound 8 from Table 1 and DcR2; compound 8 from Table 1 and DcR3; compound 8 from Table 1 and etanercept; compound 8 from Table 1 and infliximab; compound 8 from Table 1 and golimumab; compound 8 from Table 1 and certolizumab; compound 8 from Table 1 and adalimumab; compound 8 from Table 1 and R1antTNF; compound 8 from Table 1 and DMS5540; compound 8 from Table 1 and TROS; compound 8 from Table 1 and ATROSAB; compound 8 from Table 1 and humanin; compound 8 from Table 1 and a humanin analog; compound 8 from Table 1 and s14G-humanin; compound 8 from Table 1 and MTP101; compound 8 from Table 1 and elamipretide; compound 8 from Table 1 and DNA; compound 8 from Table 1 and RNA; compound 8 from Table 1 and a siRNA; compound 8 from Table 1 and FAS-targeting siRNA; compound 8 from Table 1 and FAS siRNA sense; compound 8 from Table 1 and negative siRNA sense; compound 8 from Table 1 and TNF-α targeting siRNA; compound 8 from Table 1 and NR58.3-14-3; compound 8 from Table 1 and a caspase 2 inhibitor; compound 8 from Table 1 and a caspase 3 inhibitor; compound 8 from Table 1 and a caspase 8 inhibitor; compound 8 from Table 1 and a caspase 9 inhibitor; compound 9 from Table 1 and compound 10 from Table 1; compound 9 from Table 1 and or compound 11 from Table 1; compound 9 from Table 1 and ONL1204; compound 9 from Table 1 and $H^{60}HIYLGATNYIY^{71}-NH_2$ (SEQ ID NO: 4); compound 9 from Table 1 and FAIM; compound 9 from Table 1 and NOL3; compound 9 from Table 1 and DcR1; compound 9 from Table 1 and DcR2; compound 9 from Table 1 and DcR3; compound 9 from Table 1 and etanercept; compound 9 from Table 1 and infliximab; compound 9 from Table 1 and golimumab; compound 9 from Table 1 and certolizumab; compound 9 from Table 1 and adalimumab; compound 9 from Table 1 and R1antTNF; compound 9 from Table 1 and DMS5540; compound 9 from Table 1 and TROS; compound 9 from Table 1 and ATROSAB; compound 9 from Table 1 and humanin; compound 9 from Table 1 and a humanin analog; compound 9 from Table 1 and s14G-humanin; compound 9 from Table 1 and MTP101; compound 9 from Table 1 and elamipretide; compound 9 from Table 1 and DNA; compound 9 from Table 1 and RNA; compound 9 from Table 1 and a siRNA; compound 9 from Table 1 and FAS-targeting siRNA; compound 9 from Table 1 and FAS siRNA sense; compound 9 from Table 1 and negative siRNA sense; compound 9 from Table 1 and TNF-α targeting siRNA; compound 9 from Table 1 and NR58.3-14-3; compound 9 from Table 1 and a caspase 2 inhibitor; compound 9 from Table 1 and a caspase 3 inhibitor; compound 9 from Table 1 and a caspase 8 inhibitor; compound 9 from Table 1 and a caspase 9 inhibitor; compound 10 from Table 1 and or compound 11 from Table 1; compound 10 from Table 1 and ONL1204; compound 10 from Table 1 and $H^{60}HIYLGATNYIY^{71}-NH_2$ (SEQ ID NO: 4); compound 10 from Table 1 and FAIM; compound 10 from Table 1 and NOL3; compound 10 from Table 1 and DcR1; compound 10 from Table 1 and DcR2; compound 10 from Table 1 and DcR3; compound 10 from Table 1 and etanercept; compound 10 from Table 1 and infliximab; compound 10 from Table 1 and golimumab; compound 10 from Table 1 and certolizumab; compound 10 from Table 1 and adalimumab; compound 10 from Table 1 and R1antTNF; compound 10 from Table 1 and DMS5540; compound 10 from Table 1 and TROS; compound 10 from Table 1 and ATROSAB; compound 10 from Table 1 and humanin; compound 10 from Table 1 and a humanin analog; compound 10 from Table 1 and s14G-humanin; compound 10 from Table 1 and MTP101; compound 10 from Table 1 and elamipretide; compound 10 from Table 1 and DNA; compound 10 from Table 1 and RNA; compound 10 from Table 1 and a siRNA; compound 10 from Table 1 and FAS-targeting siRNA; compound 10 from Table 1 and FAS siRNA sense; compound 10 from Table 1 and negative siRNA sense; compound 10 from Table 1 and TNF-α targeting siRNA; compound 10 from Table 1 and NR58.3-14-3; compound from Table 1 and a caspase 2 inhibitor; compound 10 from Table 1 and a caspase 3 inhibitor; compound 10 from Table 1 and a caspase 8 inhibitor; compound 10 from Table 1 and a caspase 9 inhibitor; compound 11 from Table 1 and ONL1204; compound 11 from Table 1 and $H^{60}HIYLGATNYIY^{71}-NH_2$ (SEQ ID NO: 4); compound 11 from Table 1 and FAIM; compound 11 from Table 1 and NOL3; compound 11 from Table 1 and DcR1; compound 11 from Table 1 and DcR2; compound 11 from Table 1 and DcR3; compound 11 from Table 1 and etanercept; compound 11 from Table 1 and infliximab; compound 11 from Table 1 and golimumab; compound 11 from Table 1 and certolizumab; compound 11 from Table 1 and adalimumab; compound 11 from Table 1 and R1antTNF; compound 11 from Table 1 and DMS5540; compound 11 from Table 1 and TROS; compound 11 from Table 1 and ATROSAB; compound 11 from Table 1 and humanin; compound 11 from Table 1 and a humanin analog; compound 11 from Table 1 and s14G-humanin; compound 11 from Table 1 and MTP101; compound 11 from Table 1 and elamipretide; compound 11 from Table 1 and DNA; compound 11 from Table 1 and RNA; compound 11 from Table 1 and a siRNA; compound 11 from Table 1 and FAS-targeting siRNA; compound 11 from Table 1 and FAS siRNA sense; compound 11 from Table 1 and negative siRNA sense; compound 11 from Table 1 and TNF-α targeting siRNA; compound 11 from Table 1 and NR58.3-14-3; compound 11 from Table 1 and a caspase 2 inhibitor; compound 11 from Table 1 and a caspase 3 inhibitor; compound 11 from Table 1 and a caspase 8 inhibitor; compound 11 from Table 1 and a caspase 9 inhibitor; ONL1204 and $H^{60}HIYLGATNYIY^{71}-NH_2$ (SEQ ID NO: 4); ONL1204 and FAIM; ONL1204 and NOL3; ONL1204 and DcR1; ONL1204 and DcR2; ONL1204 and DcR3; ONL1204 and etanercept; ONL1204 and infliximab; ONL1204 and golimumab; ONL1204 and certolizumab; ONL1204 and adalimumab; ONL1204 and R1antTNF; ONL1204 and DMS5540; ONL1204 and TROS; ONL1204 and ATROSAB; ONL1204 and humanin; ONL1204 and a humanin analog; ONL1204 and s14G-humanin; ONL1204 and MTP101; ONL1204 and elamipretide; ONL1204 and DNA; ONL1204 and RNA; ONL1204 and a siRNA; ONL1204 and FAS-targeting siRNA; ONL1204 and FAS siRNA sense; ONL1204 and negative siRNA sense; ONL1204 and TNF-α targeting siRNA; ONL1204 and NR58.3-14-3; ONL1204 and a caspase 2 inhibitor; ONL1204 and a caspase 3 inhibitor; ONL1204 and a caspase 8 inhibitor; ONL1204 and a caspase 9 inhibitor; $H^{60}HIYLGATNYIY^{71}-NH_2$ (SEQ ID NO: 4) and FAIM; $H^{60}HIYLGATNYIY^{71}-NH_2$ (SEQ ID NO: 4) and NOL3; $H^{60}HIYLGATNYIY^{71}-NH_2$ (SEQ ID NO: 4) and DcR1; $H^{60}HIYLGATNYIY^{71}-NH_2$ (SEQ ID NO: 4) and DcR2; $H^{60}HIYLGATNYIY^{71}-NH_2$ (SEQ ID NO: 4) and DcR3; $H^{60}HIYLGATNYIY^{71}-NH_2$ (SEQ ID NO: 4) and etanercept; $H^{60}HIYLGATNYIY^{71}-NH_2$ (SEQ ID NO: 4) and infliximab; $H^{60}HIYLGATNYIY^{71}-NH_2$ (SEQ ID NO: 4) and golimumab; $H^{60}HIYLGATNYIY^{71}-NH_2$ (SEQ ID NO: 4) and certolizumab; $H^{60}HIYLGATNYIY^{71}-NH_2$ (SEQ ID NO: 4) and adalimumab; $H^{60}HIYLGATNYIY^{71}-NH_2$ (SEQ ID NO: 4) and R1antTNF; $H^{60}HIYLGATNYIY^{71}-NH_2$ (SEQ ID NO: 4) and DMS5540; $H^{60}HIYLGATNYIY^{71}-NH_2$ (SEQ ID NO: 4) and TROS; $H^{60}HIYLGATNYIY^{71}-NH_2$ (SEQ ID NO: 4) and ATROSAB; $H^{60}HIYLGATNYIY^{71}-NH_2$ (SEQ ID NO: 4) and humanin; $H^{60}HIYLGATNYIY^{71}-NH_2$ (SEQ ID NO: 4) and a humanin analog; $H^{60}HIYLGATNYIY^{71}-NH_2$ (SEQ ID NO: 4) and s14G-humanin; $H^{60}HIYLGATNYIY^{71}-NH_2$ (SEQ ID NO: 4) and MTP101; $H^{60}HIYLGATNYIY^{71}-NH_2$ (SEQ ID NO: 4) and elamipretide; $H^{60}HIYLGATNYIY^{71}-NH_2$ (SEQ ID NO: 4) and DNA; $H^{60}HIYLGATNYIY^{71}-NH_2$ (SEQ ID NO: 4) and RNA; $H^{60}HIYLGATNYIY^{71}-NH_2$ (SEQ ID NO: 4) and a siRNA; $H^{60}HIYLGATNYIY^{71}-NH_2$ (SEQ ID NO: 4) and FAS-targeting siRNA; $H^{60}HIYLGATNYIY^{71}-NH_2$ (SEQ ID NO: 4) and FAS siRNA sense; $H^{60}HIYLGATNYIY^{71}-NH_2$ (SEQ ID NO: 4) and negative siRNA sense; $H^{60}HIYLGATNYIY^{71}-NH_2$ (SEQ ID NO: 4) and TNF-α targeting siRNA; $H^{60}HIYLGATNYIY^{71}-NH_2$ (SEQ ID NO: 4) and NR58.3-14-3; $H^{60}HIYLGATNYIY^{71}-NH_2$ (SEQ ID NO: 4) and a caspase 2 inhibitor; $H^{60}HIYLGATNYIY^{71}-NH_2$ (SEQ ID NO: 4) and a caspase 3 inhibitor; $H^{60}HIYLGATNYIY^{71}-NH_2$ (SEQ ID NO: 4) and a caspase 8 inhibitor; $H^{60}HIYLGATNYIY^{71}-NH_2$ (SEQ ID NO: 4) and a caspase 9 inhibitor; FAIM and NOL3; FAIM and DcR1; FAIM and DcR2; FAIM and DcR3; FAIM and etanercept; FAIM and infliximab; FAIM and golimumab; FAIM and certolizumab; FAIM and adalimumab; FAIM and R1antTNF; FAIM and DMS5540; FAIM and TROS; FAIM and ATROSAB; FAIM and humanin; FAIM and a humanin analog; FAIM and s14G-humanin; FAIM and MTP101; FAIM and elamipretide; FAIM and DNA; FAIM and RNA; FAIM and a siRNA; FAIM and FAS-targeting siRNA; FAIM and FAS siRNA sense; FAIM and negative siRNA sense; FAIM and TNF-α targeting siRNA; FAIM and NR58.3-14-3; FAIM and a caspase 2 inhibitor; FAIM and a caspase 3 inhibitor; FAIM and a caspase 8 inhibitor; FAIM and a caspase 9 inhibitor; NOL3 and DcR1; NOL3 and DcR2; NOL3 and DcR3; NOL3 and etanercept; NOL3 and infliximab; NOL3 and golimumab; NOL3 and certolizumab; NOL3 and adalimumab; NOL3 and R1antTNF; NOL3 and DMS5540; NOL3 and TROS; NOL3 and ATROSAB; NOL3 and humanin; NOL3 and a humanin analog; NOL3 and s14G-humanin; NOL3 and MTP101; NOL3 and elamipretide; NOL3 and DNA; NOL3 and RNA; NOL3 and a siRNA; NOL3 and FAS-targeting siRNA; NOL3 and FAS siRNA sense; NOL3 and negative siRNA sense; NOL3 and TNF-α targeting siRNA; NOL3 and NR58.3-14-3; NOL3 and a caspase 2 inhibitor; NOL3 and a caspase 3 inhibitor; NOL3 and a caspase 8 inhibitor; NOL3 and a caspase 9 inhibitor; DcR1 and DcR2; DcR1 and DcR3; DcR1 and etanercept; DcR1 and infliximab; DcR1 and golimumab; DcR1 and certolizumab; DcR1 and adalimumab; DcR1 and R1antTNF; DcR1 and DMS5540; DcR1 and TROS; DcR1 and ATROSAB; DcR1 and humanin; DcR1 and a humanin analog; DcR1 and s14G-humanin; DcR1 and MTP101; DcR1 and elamipretide; DcR1 and DNA; DcR1 and RNA; DcR1 and a siRNA; DcR1 and FAS-targeting siRNA; DcR1 and FAS siRNA sense; DcR1 and negative siRNA sense; DcR1 and TNF-α targeting siRNA; DcR1 and NR58.3-14-3; DcR1 and a caspase 2 inhibitor; DcR1 and a caspase 3 inhibitor; DcR1 and a caspase 8 inhibitor; DcR1 and a caspase 9 inhibitor; DcR2 and DcR3; DcR2 and etanercept; DcR2 and infliximab; DcR2 and golimumab; DcR2 and certolizumab; DcR2 and adalimumab; DcR2 and R1antTNF; DcR2 and DMS5540; DcR2 and TROS; DcR2 and ATROSAB; DcR2 and humanin; DcR2 and a humanin analog; DcR2 and s14G-humanin; DcR2 and MTP101; DcR2 and elamipretide; DcR2 and DNA; DcR2 and RNA; DcR2 and a siRNA; DcR2 and FAS-targeting siRNA; DcR2 and FAS siRNA sense; DcR2 and negative siRNA sense; DcR2 and TNF-α targeting siRNA; DcR2 and NR58.3-14-3; DcR2 and a caspase 2 inhibitor; DcR2 and a caspase 3 inhibitor; DcR2 and a caspase 8 inhibitor; DcR2 and a caspase 9 inhibitor; DcR3 and etanercept; DcR3 and infliximab; DcR3 and golimumab; DcR3 and certolizumab; DcR3 and adalimumab; DcR3 and R1antTNF; DcR3 and DMS5540; DcR3 and TROS; DcR3 and ATROSAB; DcR3 and humanin; DcR3 and a humanin analog; DcR3 and s14G-humanin; DcR3 and MTP101; DcR3 and elamipretide; DcR3 and DNA; DcR3 and RNA; DcR3 and a siRNA; DcR3 and FAS-targeting siRNA; DcR3 and FAS siRNA sense; DcR3 and negative siRNA sense; DcR3 and TNF-α targeting siRNA; DcR3 and NR58.3-14-3; DcR3 and a caspase 2 inhibitor; DcR3 and a caspase 3 inhibitor; DcR3 and a caspase 8 inhibitor; DcR3 and a caspase 9 inhibitor; etanercept and infliximab; etanercept and golimumab; etanercept and certolizumab; etanercept and adalimumab; etanercept and R1antTNF; etanercept and DMS5540; etanercept and TROS; etanercept and ATROSAB; etanercept and humanin; etanercept and a humanin analog; etanercept and s14G-humanin; etanercept and MTP101; etanercept and elamipretide; etanercept and DNA; etanercept and RNA; etanercept and a siRNA; etanercept and FAS-targeting siRNA; etanercept and FAS siRNA sense; etanercept and negative siRNA sense; etanercept and TNF-α targeting siRNA; etanercept and NR58.3-14-3; etanercept and a caspase 2 inhibitor; etanercept and a caspase 3 inhibitor; etanercept and a caspase 8 inhibitor; etanercept and a caspase 9 inhibitor; infliximab and golimumab; infliximab and certolizumab; infliximab and adalimumab; infliximab and R1antTNF; infliximab and DMS5540; infliximab and TROS; infliximab and ATROSAB; infliximab and humanin; infliximab and a humanin analog; infliximab and s14G-humanin; infliximab and MTP101; infliximab and elamipretide; infliximab and DNA; infliximab and RNA; infliximab and a siRNA; infliximab and FAS-targeting SIRNA; infliximab and FAS siRNA sense; infliximab and negative siRNA sense; infliximab and TNF-α targeting siRNA; infliximab and NR58.3-14-3; infliximab and a caspase 2 inhibitor; infliximab and a caspase 3 inhibitor; infliximab and a caspase 8 inhibitor; infliximab and a caspase 9 inhibitor; golimumab and certolizumab; golimumab and adalimumab; golimumab and R1antTNF; golimumab and DMS5540; golimumab and TROS; golimumab and ATROSAB; golimumab and humanin; golimumab and a humanin analog; golimumab and s14G-humanin; golimumab and MTP101; golimumab and elamipretide; golimumab and DNA; golimumab and RNA; golimumab and a siRNA; golimumab and FAS-targeting siRNA; golimumab and FAS siRNA sense; golimumab and negative siRNA sense; golimumab and TNF-α targeting siRNA; golimumab and NR58.3-14-3; golimumab and a caspase 2 inhibitor; golimumab and a caspase 3 inhibitor; golimumab and a caspase 8 inhibitor; golimumab and a caspase 9 inhibitor; certolizumab and adalimumab; certolizumab and R1antTNF; certolizumab and DMS5540; certolizumab and TROS; certolizumab and ATROSAB; certolizumab and humanin; certolizumab and a humanin analog; certolizumab and s14G-humanin; certolizumab and MTP101; certolizumab and elamipretide; certolizumab and DNA; certolizumab and RNA; certolizumab and a siRNA; certolizumab and FAS-targeting siRNA; certolizumab and FAS siRNA sense; certolizumab and negative siRNA sense; certolizumab and TNF-α targeting siRNA; certolizumab and NR58.3-14-3; certolizumab and a caspase 2 inhibitor; certolizumab and a caspase 3 inhibitor; certolizumab and a caspase 8 inhibitor; certolizumab and a caspase 9 inhibitor; adalimumab and R1antTNF; adalimumab and DMS5540; adalimumab and TROS; adalimumab and ATROSAB; adalimumab and humanin; adalimumab and a humanin analog; adalimumab and s14G-humanin; adalimumab and MTP101; adalimumab and elamipretide; adalimumab and DNA; adalimumab and RNA; adalimumab and a siRNA; adalimumab and FAS-targeting siRNA; adalimumab and FAS siRNA sense; adalimumab and negative siRNA sense; adalimumab and TNF-α targeting siRNA; adalimumab and NR58.3-14-3; adalimumab and a caspase 2 inhibitor; adalimumab and a caspase 3 inhibitor; adalimumab and a caspase 8 inhibitor; adalimumab and a caspase 9 inhibitor; R1antTNF and DMS5540; R1antTNF and TROS; R1antTNF and ATROSAB; R1antTNF and humanin; R1antTNF and a humanin analog; R1antTNF and s14G-humanin; R1antTNF and MTP101; R1antTNF and elamipretide; R1antTNF and DNA; R1antTNF and RNA; R1antTNF and a siRNA; R1antTNF and FAS-targeting siRNA; R1antTNF and FAS siRNA sense; R1antTNF and negative siRNA sense; R1antTNF and TNF-α targeting siRNA; R1antTNF and NR58.3-14-3; R1antTNF and a caspase 2 inhibitor; R1antTNF and a caspase 3 inhibitor; R1antTNF and a caspase 8 inhibitor; R1antTNF and a caspase 9 inhibitor; DMS5540 and TROS; DMS5540 and ATROSAB; DMS5540 and humanin; DMS5540 and a humanin analog; DMS5540 and s14G-humanin; DMS5540 and MTP101; DMS5540 and elamipretide; DMS5540 and DNA; DMS5540 and RNA; DMS5540 and a siRNA; DMS5540 and FAS-targeting siRNA; DMS5540 and FAS siRNA sense; DMS5540 and negative siRNA sense; DMS5540 and TNF-α targeting siRNA; DMS5540 and NR58.3-14-3; DMS5540 and a caspase 2 inhibitor; DMS5540 and a caspase 3 inhibitor; DMS5540 and a caspase 8 inhibitor; DMS5540 and a caspase 9 inhibitor; TROS and ATROSAB; TROS and humanin; TROS and a humanin analog; TROS and s14G-humanin; TROS and MTP101; TROS and elamipretide; TROS and DNA; TROS and RNA; TROS and a siRNA; TROS and FAS-targeting siRNA; TROS and FAS siRNA sense; TROS and negative siRNA sense; TROS and TNF-α targeting SiRNA; TROS and NR58.3-14-3; TROS and a caspase 2 inhibitor; TROS and a caspase 3 inhibitor; TROS and a caspase 8 inhibitor; TROS and a caspase 9 inhibitor; ATROSAB and humanin; ATROSAB and a humanin analog; ATROSAB and s14G-humanin; ATROSAB and MTP101; ATROSAB and elamipretide; ATROSAB and DNA; ATROSAB and RNA; ATROSAB and a siRNA; ATROSAB and FAS-targeting siRNA; ATROSAB and FAS siRNA sense; ATROSAB and negative siRNA sense; ATROSAB and TNF-α targeting siRNA; ATROSAB and NR58.3-14-3; ATROSAB and a caspase 2 inhibitor; ATROSAB and a caspase 3 inhibitor; ATROSAB and a caspase 8 inhibitor; ATROSAB and a caspase 9 inhibitor; humanin and a humanin analog; humanin and s14G-humanin; humanin and MTP101; humanin and elamipretide; humanin and DNA; humanin and RNA; humanin and a siRNA; humanin and FAS-targeting siRNA; humanin and FAS siRNA sense; humanin and negative siRNA sense; humanin and TNF-α targeting siRNA; humanin and NR58.3-14-3; humanin and a caspase 2 inhibitor; humanin and a caspase 3 inhibitor; humanin and a caspase 8 inhibitor; humanin and a caspase 9 inhibitor; a humanin analog and s14G-humanin; a humanin analog and MTP101; a humanin analog and elamipretide; a humanin analog and DNA; a humanin analog and RNA; a humanin analog and a siRNA; a humanin analog and FAS-targeting siRNA; a humanin analog and FAS siRNA sense; a humanin analog and negative siRNA sense; a humanin analog and TNF-α targeting siRNA; a humanin analog and NR58.3-14-3; a humanin analog and a caspase 2 inhibitor; a humanin analog and a caspase 3 inhibitor; a humanin analog and a caspase 8 inhibitor; a humanin analog and a caspase 9 inhibitor; s14G-humanin and MTP101; s14G-humanin and elamipretide; s14G-humanin and DNA; s14G-humanin and RNA; s14G-humanin and a siRNA; s14G-humanin and FAS-targeting siRNA; s14G-humanin and FAS siRNA sense; s14G-humanin and negative siRNA sense; s14G-humanin and TNF-α targeting siRNA; s14G-humanin and NR58.3-14-3; s14G-humanin and a caspase 2 inhibitor; s14G-humanin and a caspase 3 inhibitor; s14G-humanin and a caspase 8 inhibitor; s14G-humanin and a caspase 9 inhibitor; MTP101 and elamipretide; MTP101 and DNA; MTP101 and RNA; MTP101 and a siRNA; MTP101 and FAS-targeting siRNA; MTP101 and FAS siRNA sense; MTP101 and negative siRNA sense; MTP101 and TNF-α targeting siRNA; MTP101 and NR58.3-14-3; MTP101 and a caspase 2 inhibitor; MTP101 and a caspase 3 inhibitor; MTP101 and a caspase 8 inhibitor; MTP101 and a caspase 9 inhibitor; elamipretide and DNA; elamipretide and RNA; elamipretide and a siRNA; elamipretide and FAS-targeting siRNA; elamipretide and FAS siRNA sense; elamipretide and negative siRNA sense; elamipretide and TNF-α targeting siRNA; elamipretide and NR58.3-14-3; elamipretide and a caspase 2 inhibitor; elamipretide and a caspase 3 inhibitor; elamipretide and a caspase 8 inhibitor; elamipretide and a caspase 9 inhibitor; DNA and RNA; DNA and a siRNA; DNA and FAS-targeting siRNA; DNA and FAS siRNA sense; DNA and negative siRNA sense; DNA and TNF-α targeting siRNA; DNA and NR58.3-14-3; DNA and a caspase 2 inhibitor; DNA and a caspase 3 inhibitor; DNA and a caspase 8 inhibitor; DNA and a caspase 9 inhibitor; RNA and a siRNA; RNA and FAS-targeting siRNA; RNA and FAS siRNA sense; RNA and negative siRNA sense; RNA and TNF-α targeting siRNA; RNA and NR58.3-14-3; RNA and a caspase 2 inhibitor; RNA and a caspase 3 inhibitor; RNA and a caspase 8 inhibitor; RNA and a caspase 9 inhibitor; a siRNA and FAS-targeting siRNA; a siRNA and FAS siRNA sense; a siRNA and negative siRNA sense; a siRNA and TNF-α targeting siRNA; a siRNA and NR58.3-14-3; a siRNA and a caspase 2 inhibitor; a siRNA and a caspase 3 inhibitor; a siRNA and a caspase 8 inhibitor; a siRNA and a caspase 9 inhibitor; FAS-targeting siRNA and FAS siRNA sense; FAS-targeting siRNA and negative siRNA sense; FAS-targeting siRNA and TNF-α targeting siRNA; FAS-targeting siRNA and NR58.3-14-3; FAS-targeting siRNA and a caspase 2 inhibitor; FAS-targeting siRNA and a caspase 3 inhibitor; FAS-targeting siRNA and a caspase 8 inhibitor; FAS-targeting siRNA and a caspase 9 inhibitor; FAS siRNA sense and negative siRNA sense; FAS siRNA sense and TNF-α targeting siRNA; FAS siRNA sense and NR58.3-14-3; FAS siRNA sense and a caspase 2 inhibitor; FAS siRNA sense and a caspase 3 inhibitor; FAS siRNA sense and a caspase 8 inhibitor; FAS siRNA sense and a caspase 9 inhibitor; negative siRNA sense and TNF-α targeting siRNA; negative siRNA sense and NR58.3-14-3; negative siRNA sense and a caspase 2 inhibitor; negative siRNA sense and a caspase 3 inhibitor; negative siRNA sense and a caspase 8 inhibitor; negative siRNA sense and a caspase 9 inhibitor; TNF-α targeting siRNA and NR58.3-14-3; TNF-α targeting siRNA and a caspase 2 inhibitor; TNF-α targeting siRNA and a caspase 3 inhibitor; TNF-α targeting siRNA and a caspase 8 inhibitor; TNF-α targeting siRNA and a caspase 9 inhibitor; NR58.3-14-3 and a caspase 2 inhibitor; NR58.3-14-3 and a caspase 3; NR58.3-14-3 and a caspase 8; NR58.3-14-3 and a caspase 9; a caspase 2 inhibitor and a caspase 3 inhibitor; a caspase 2 inhibitor and a caspase 8 inhibitor; a caspase 2 inhibitor and a caspase 9 inhibitor; a caspase 3 inhibitor and a caspase 8 inhibitor; a caspase 3 inhibitor and a caspase 9 inhibitor; a caspase 8 inhibitor and a caspase 9 inhibitor; or MET12 (SEQ ID NO: 3) and Peptide 6 (SEQ ID NO: 1).

With respect to any relevant structural representation, such as Formula 1, I, 2, D, E, or F, Neu-H is a neurotrophic agent, such as a neurotrophic agent recited above.

With respect to any relevant structural representation, such as Formula 1, A, G, H, J, or K, FAS-H is a FAS/FASL inhibitor, such as a FAS/FASL inhibitor recited above.

With respect to any relevant structural representation, such as Formula I, B, G, M, N, or O, TNF-H is a TNF-α/TNFR inhibitor, such as a TNF-α/TNFR inhibitor recited above.

With respect to any relevant structural representation, such as Formula 2, H, M, P, Q, or R, Mit-H is a mitochondrial peptide, such as a mitochondrial peptide recited above.

With respect to any relevant structural representation, such as Formula A, B, D, P, S, or T, Nuc-H is an oligonucleotide, such as an oligonucleotide recited above.

With respect to any relevant structural representation, such as Formula E, J, N, Q, S, or U, CK-H is a chemokine inhibitor, such as a chemokine inhibitor recited above.

With respect to any relevant structural representation, such as Formula F, K, O, R, T, or U, CAS-H is a cysteine-aspartic protease (caspase) inhibitor, such as a caspase inhibitor recited above.

With respect to any relevant structural representation, i.e. a structure including L, such as 1, I, 2, 3, 4, 5, 6, 7, A, B, C, C1, D, E, F, G, H, J, K, M, N, O, P, Q, R, S, T, U, II, IID, 3D, 4D, 5D, 6D, or 7D, (Formulas C, II, IID, 3-7 and 3D-7D are depicted below), L is a linking group represented by the empirical formula $C_aH_bO_cN_d$ or $C_aH_bO_c$.

With respect to any L, a is 1, 2, 3, 4, 5, 6, 7, 8, 9, 10, 11, 12, 13, 14, 15, 16, 17, 18, 19, or 20. In some embodiments, a is 1-5, 5-10, 10-15, 15-20, 1-10, or 10-20.

With respect to any L, b is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43. In some embodiments, b is 1-10, 10-20, 20-30, 30-40, 40-43, 1-15, 15-30, or 30-43.

With respect to any L, cis 0, 1, 2, 3, 4, 5, 6, 7, 8, 9, or 10. In some embodiments, c is 0-2, 2-4, 4-6, 6-8, 8-10, 0-3, 3-6, or 6-10.

With respect to any L, d is 0, 1, or 2. In some embodiments, d is 0. In some embodiments, d is 1. In some embodiments, d is 2.

In some embodiments, L may be represented by Formula L-1, L-2, L-3, L-4, L-5, L-6, L-7, or L-8:

Formula L-1

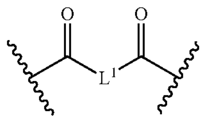

Formula L-2

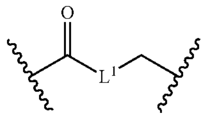

Formula L-3

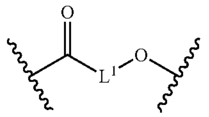

Formula L-4

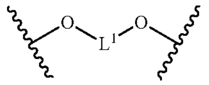

Formula L-5

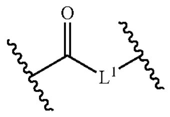

Formula L-6

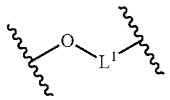

Formula L-7

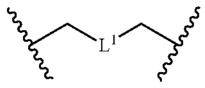

,

Formula L-8

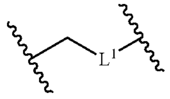

With respect to any relevant structural representation, such as Formula L-1, L-2, L-3, L-4, L-5, L-6, L-7, or L-8, $L^1$ may be represented by the empirical formula $C_eH_fO_gN_h$ or $C_eH_fO_g$.

With respect to any $L^1$, e is 1, 2, 3, 4, 5, 6, 7, 8, 9, 10, 11, 12, 13, 14, 15, 16, 17, or 18. In some embodiments, e is 1-5, 5-10, 10-15, 15-20, 1-10, or 10-18.

With respect to any $L^1$, f is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38. In some embodiments, f is 1-10, 10-20, 20-30, 30-38, 1-15, 15-30, or 30-38.

With respect to any $L^1$, g is 0, 1, 2, 3, 4, 5, 6, 7, or 8. In some embodiments, g is 0-2, 2-4, 4-6, 6-8, 0-3, 3-6, or 6-8.

With respect to any $L^1$, h is 0, 1, or 2. In some embodiments, h is 0. In some embodiments, h is 1. In some embodiments, h is 2.

With respect to any relevant structural representation, such as Formula L-1, L-2, L-3, L-4, L-5, L-6, L-7, or L-8, in some embodiments $L^1$ may be:

[Formula $L^1$-1]

$$-(CH_2)_i-(OCH_2CH_2)_j-O-(CH_2)_k-,$$

[Formula $L^1$-2]

$$-(CH_2)_i-(OCH_2CH_2)_j-O-CONH-(CH_2)_k-,$$

[Formula $L^1$-3]

$$-(C_iH_{2i})-(OCH_2CH_2)_j-O-(C_kH_{2k})-,\text{ or}$$

[Formula $L^1$-4]

$$-(C_iH_{2i})-(OCH_2CH_2)_j-O-CONH-(C_kH_{2k})-.$$

With respect to any relevant structural representation, such as Formula $L^1$-1, $L^1$-2, $L^1$-3, or $L^1$-4, i is 0, 1, 2, 3, or 4.

With respect to any relevant structural representation, such as Formula $L^1$-1, $L^1$-2, $L^1$-3, or $L^1$-4, j is 0, 1, 2, 3, 4, or 5.

With respect to any relevant structural representation, such as Formula $L^1$-1, $L^1$-2, $L^1$-3, or $L^1$-4, k is 0, 1, 2, 3, or 4.

A sustained delivery component is the portion of the drug delivery system that allows the drug to remain in the body for a sustained period of time, e.g. long beyond the time that it takes for the drug to be metabolized or passed out of the body. Typically, a sustained delivery component is an implant, such as a solid implant, that works by encapsulating or otherwise entrapping the drug into the implant. If the implant is biodegradable or bioerodible, the drug may be released as the implant biodegrades or bioerodes. The implant may also be porous so that, over a period of time, the drug may diffuse out of the implant. Biodegradable or bioerodible implants may be porous or non-porous. Typically, non-biodegradable or non-bioerodible implants are porous, and the drug is released by diffusion. However, other mechanisms may operate, such as an osmotic pump.

The drug may be physically trapped in the sustained delivery component and/or may be covalently bonded to a molecule that is part of the sustained delivery component.

Typical examples of biodegradable materials for porous or non-porous biodegradable implants generally include, silica-based materials, or organic biodegradable materials, such as polymers comprising poly (D,L-lactic acid) (PLA) and poly (D,L-lactic-co-glycolic acid) (PLGA), polyesteramide (PEA, DSM chemical), and polycaprolactone (PCL); hydrogels, such as polyvinyl alcohols (PVA), PEG amines, PEG-N-hydroxysuccinamide esters (like Ocular Therapeutix) and the like; collagen based materials (e.g. Euclid systems); or a combination thereof.

There are a number of suitable silica based sustained delivery components.

One type of silica based sustained delivery component includes a silica hydrogel composite obtainable by mixing silica particles, comprising an encapsulated drug, with a silica sol, wherein obtained hydrogel composite is shear-thinning. This type of delivery system is an injectable, all-silica-based microparticle-silica hydrogel controlled release system which reduces the burst remarkably with different types of encapsulated therapeutic and biologically active agents. Detailed descriptions of this type of silica based sustained delivery component, and how they are made, are found in U.S. Pat. No. 9,949,922, issued on Apr. 24, 2018 to Jokinen, et al., which is incorporated by reference herein in its entirety.

Another type of silica based sustained delivery component includes flowing silica compositions and gels comprising a drug which are obtainable by a method for producing a flowing silica composition including a sol-gel transfer, where redispersion is carried out. The redispersion includes adding, after having reached gel point of the sol-gel transfer, liquid into the gel formed by the sol-gel transfer, and the addition being made within a sufficiently short time period after reaching the gel point, to result, after mixing of the gel and the liquid, in a rheologically homogenous flowing silica composition, which is and remains injectable as such, or by short stirring <30 s, through a thin 22G needle. These flowing and injectable sustained delivery silica compositions may increase the stability and preserve the activity of encapsulated therapeutic agents. Detailed descriptions of this type of silica based sustained delivery component, and how it is made, is found in U.S. patent application No. 20140057996, published Feb. 27, 2014 by Jokinen, et al., which is incorporated by reference herein in its entirety.

Another type of silica based sustained delivery component comprises a composition comprising a bioerodible porous silicon-based carrier material wherein the carrier material carries a drug and at least one amorphous sugar, optionally further comprising a crystallization inhibitor. These delivery systems comprise loading biomolecules into the pores of the silica carrier material, thus stabilizing the biomolecules. However, these systems may also be used for small molecule therapeutic compounds. Detailed descriptions of this type of silica based sustained delivery component, and how it is made, is found in U.S. Pat. No. 9,603,801, issued on Mar. 28, 2017 to Barnett, et al., which is incorporated by reference herein in its entirety.

Another type of silica based sustained delivery component includes bioerodible devices, such as implants for delivering drugs in a controlled manner. The devices comprise a porous silicon-based carrier material impregnated or loaded with the drug. These particular silicon carrier materials comprise at least one large molecule therapeutic agent disposed in the pores of the carrier material. It is believed that the loading of large therapeutic molecule into the pores of the carrier material stabilizes the large molecules. In many embodiments, the large molecule is a protein and the pores have an average size between about 15 nm to about 40 nm, and the protein has a molecular weight from about 100,000 amu to about 200,000 amu. Detailed descriptions of this type of silica based sustained delivery component, and how it is made, is found in U.S. Pat. No. 9,808,421, issued on Nov. 7, 2017, to Ashton et al., U.S. Pat. No. 9,333,173 issued on May 10, 2016 to Ashton et al., and United States Patent Publication No. 20140271764 published on Sep. 28, 2014 by Ashton, et al., all of which are incorporated by reference herein in its entirety.

The sustained delivery component may have any suitable mass, such as about 10 μg-100 mg, about 10-20 μg, about 20-30 μg, about 30-40 μg, about 40-50 μg, about 50-60 μg, about 60-70 μg, about 70-80 μg, about 80-90 μg, about 90-100 μg, about 100-200 μg, about 200-300 μg, about 300-400 μg, about 400-500 μg, about 500-600 μg, about 600-700 μg, about 700-800 μg, about 800-900 μg, about 900-1,000 μg, about 1-2 mg, about 2-3 mg, about 3-4 mg, about 4-5 mg, about 5-6 mg, about 6-7 mg, about 7-8 mg, about 8-9 mg, about 9-10 mg, about 10-20 mg, about 20-30 mg, about 30-40 mg, about 40-50 mg, about 50-60 mg, about 60-70 mg, about 70-80 mg, about 80-90 mg, about 90-100 mg, about 100-200 mg, about 200-300 mg, about 300-400 mg, about 400-500 mg, about 500-600 mg, about 600-700 mg, about 700-800 mg, about 800-900 mg, about 900-1,000 mg, about 1-2 g, about 2-3 g, about 3-4 g, about 4-5 g, about 5-6 g, about 6-7 g, about 7-8 g, about 8-9 g, about 9-10 g, about 10-20 g, about 20-30 g, about 30-40 g, about 40-50 g, about 50-60 g, about 60-70 g, about 70-80 g, about 80-90 g, about 90-100 g, about 100-200 g, about 200-300 g, about 300-400 g, about 400-500 g, about 500-600 g, about 600-700 g, about 700-800 g, about 800-900 g, about 900-1,000 g, about 10-100 μg, about 100-1,000 μg, about 1-10 mg, about 10-100 mg, about 100-1,000 mg, about 1-10 g, about 10-100 g, or about 100-1,000 g. Ranges above which are about 1 g or less, or 100 mg or less, may be of interest for drug delivery systems delivered onto or into the eye.

The sustained delivery component may be any suitable percentage of the implant, such as about 1-99 wt %, about 1-10 wt %, about 10-20 wt %, about 20-30 wt %, about 30-40 wt %, about 40-50 wt %, about 50-60 wt %, about 60-70 wt %, about 70-80 wt %, about 80-90 wt %, about 90-99 wt %, about 1-30 wt %, about 30-65 wt %, about 65-99 wt %, about 1-50 wt %, or about 50-99 wt %.

The drug delivery system may be of any suitable size, such as about 10 μg-100 mg, about 10-20 μg, about 20-30 μg, about 30-40 μg, about 40-50 μg, about 50-60 μg, about 60-70 μg, about 70-80 μg, about 80-90 μg, about 90-100 μg, about 100-200 μg, about 200-300 μg, about 300-400 μg, about 400-500 μg, about 500-600 μg, about 600-700 μg, about 700-800 μg, about 800-900 μg, about 900-1,000 μg, about 1-2 mg, about 2-3 mg, about 3-4 mg, about 4-5 mg, about 5-6 mg, about 6-7 mg, about 7-8 mg, about 8-9 mg, about 9-10 mg, about 10-20 mg, about 20-30 mg, about 30-40 mg, about 40-50 mg, about 50-60 mg, about 60-70 mg, about 70-80 mg, about 80-90 mg, about 90-100 mg, about 100-200 mg, about 200-300 mg, about 300-400 mg, about 400-500 mg, about 500-600 mg, about 600-700 mg, about 700-800 mg, about 800-900 mg, about 900-1,000 mg, about 1-2 g, about 2-3 g, about 3-4 g, about 4-5 g, about 5-6 g, about 6-7 g, about 7-8 g, about 8-9 g, about 9-10 g, about 10-20 g, about 20-30 g, about 30-40 g, about 40-50 g, about 50-60 g, about 60-70 g, about 70-80 g, about 80-90 g, about 90-100 g, about 100-200 g, about 200-300 g, about 300-400 g, about 400-500 g, about 500-600 g, about 600-700 g, about 700-800 g, about 800-900 g, about 900-1,000 g, about 10-100 μg, about 100-1,000 μg, about 1-10 mg, about 10-100 mg, about 100-1,000 mg, about 1-10 g, about 10-100 g, or about 100-1,000 g. Ranges above which are about 1 g or less, or 100 mg or less, may be of interest for drug delivery systems delivered onto or into the eye.

Typical examples of non-biodegradable or non-bioerodible materials for implants include silicones or PVA as semipermeable membranes (like Psivida).

Other potential sustained delivery components could be based upon cell-based approaches like encapsulated cell technology; and reservoir type approaches (forsight4; Replenish).

The neurotrophic agent, the FAS/FASL inhibitor, the TNF-α/TNFR inhibitor and/or the mitochondrial peptide may, or may not, be covalently attached to the sustained delivery component.

In some embodiments, the neurotrophic agent is covalently attached to the sustained delivery component. In some embodiments, the neurotrophic agent is not covalently attached to the sustained delivery component.

In some embodiments, the FAS/FASL inhibitor is covalently attached to the sustained delivery component. In some embodiments, the FAS/FASL inhibitor is not covalently attached to the sustained delivery component.

In some embodiments, the TNF-α/TNFR inhibitor is covalently attached to the sustained delivery component. In some embodiments, the TNF-α/TNFR inhibitor is not covalently attached to the sustained delivery component.

In some embodiments, the mitochondrial peptide is covalently attached to the sustained delivery component. In some embodiments, the mitochondrial peptide is not covalently attached to the sustained delivery component.

In some embodiments, the oligonucleotide is covalently attached to the sustained delivery component. In some embodiments, the oligonucleotide is not covalently attached to the sustained delivery component.

For example, a neurotrophic agent may be covalently attached to the sustained delivery component using a compound represented by a formula:

Formula 3

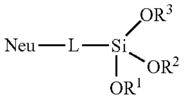

wherein Neu-H is a neurotrophic agent, such as a neurotrophic agent recited above.

An oligonucleotide may be covalently attached to the sustained delivery component using a compound represented by a formula:

Formula C

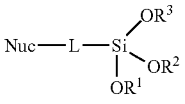

wherein Nuc-H is an oligonucleotide, such as an oligonucleotide recited above.

A FAS/FASL inhibitor may be covalently attached to the sustained delivery component using a compound represented by a formula:

Formula 4

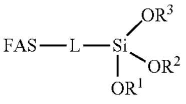

wherein FAS-H is a FAS/FASL inhibitor, such as a FAS/FASL inhibitor recited above.

A TNF-α/TNFR inhibitor may be covalently attached to the sustained delivery component using a compound represented by a formula:

Formula II

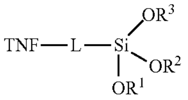

wherein TNF-H is a TNF-α/TNFR inhibitor, such as a TNF-α/TNFR inhibitor recited above.

A mitochondrial peptide may be covalently attached to the sustained delivery component using a compound represented by a formula:

Formula 5

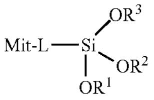

wherein Mit-H is a mitochondrial peptide, such as a mitochondrial peptide recited above.

A chemokine inhibitor may be covalently attached to the sustained delivery component using a compound represented by a formula:

Formula 6

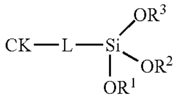

wherein CK-H is a chemokine inhibitor, such as a chemokine inhibitor recited above.

A cysteine-aspartic protease (caspase) inhibitor (depicted as "CAS" below) may be covalently attached to the sustained delivery component using a compound represented by a formula:

Formula 7

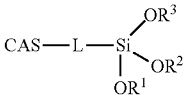

wherein CAS-H is a cysteine-aspartic protease (caspase) inhibitor, such as a caspase inhibitor recited above.

With respect to any relevant structural representation, such as Formula C, 3, 4, II, 5, 6, or 7, $R^1$ is independently H or $C_{1-6}$ alkyl, such as $CH_3$, $C_2$ alkyl, $C_3$ alkyl, $C_4$ alkyl, $C_5$ alkyl, or $C_6$ alkyl.

With respect to any relevant structural representation, such as Formula C, 3, 4, II, 5, 6, or 7, $R^2$ is independently H or $C_{1-6}$ alkyl, such as $CH_3$, $C_2$ alkyl, $C_3$ alkyl, $C_4$ alkyl, $C_5$ alkyl, or $C_6$ alkyl.

With respect to any relevant structural representation, such as Formula C, 3, 4, II, 5, 6, or 7, or a compound below, and $R^3$ is independently H or $C_{1-6}$ alkyl, such as $CH_3$, $C_2$ alkyl, $C_3$ alkyl, $C_4$ alkyl, $C_5$ alkyl, or $C_6$ alkyl.

An example of a compound of Formula 3 is: VGDGGLFEKKL-PEG-$Si(OH)_3$ ("VGDGGLFEKKL" disclosed as SEQ ID NO: 1) or VGDGGLFEKKL-PEG-$SiOR^1OR^2OR^3$ ("VGDGGLFEKKL" disclosed as SEQ ID NO: 1) wherein PEG is a polyethylene glycol chain (e.g. $—(OCH_2CH_2)_n—$, where n is 1, 2, 3, 4, 5, 6, 7, 8, 9, 10, etc.). In the body, the ester bond can hydrolyze to release VGDGGLFEKKL (SEQ ID NO: 1).

The $SiOR^1OR^2OR^3$ group of Formulas C or 3-5 may be covalently bonded to the silica of a silica based drug delivery system, e.g. to form compounds represented by Formulas C1, 3D, 4D, or 5D, wherein D is a sustained delivery component comprising the Si of the $SiOR^1OR^2OR^3$ of Formula C, 3, 4, 5, 6, or 7.

Nuc—L—D Formula C1

Neu—L—D Formula 3D

FAS—L—D Formula 4D

TNF—L—D Formula IID

Mit—L—D Formula 5D

CK—L—D Formula 6D

CAS—L—D Formula 7D

The drug delivery system may optionally further contain an antioxidant, such as ascorbyl palmitate, butylated hydroxyanisole, butylated hydroxytoluene, potassium metabisulfite, propyl gallate, sodium metabisulfite, sodium thiosulfate, vitamin E, 3,4-dihydroxybenzoic acid, cysteine, etc.

For some treatments, the drug delivery system may be injected at a reduced temperature, such as about −7° C. to about 17° C., about −7° C. to about 0° C., about 0° C. to about 5° C., about 5° C. to about 10° C., about 10° C. to about 17° C., etc., to improve the performance of the drug delivery system. For example, this may provide more sustained delivery of the drug, more consistent levels of the drug, improved efficacy of the drug, etc.

A drug delivery system containing a neurotrophic agent, a FAS/FASL inhibitor, a TNF-α/TNFR inhibitor, a mitochondrial peptide; an oligonucleotide a chemokine inhibitor, or a cysteine-aspartic protease (caspase) inhibitor; and an optional sustained delivery component (referred to herein as "subject drug delivery system") may be administered to a mammal, such as a human, by any suitable method, such as by injection or surgical implantation into any part of the body, oral administration, or topical application to the eye or skin. In some embodiments, a subject drug delivery system is injected or otherwise implanted in an eye, including: the anterior chamber, the posterior chamber, the subconjunctival space or subtenon's space. In some embodiments, the subject drug delivery system may be injected subcutaneously, or directly into a tissue such as the heart, brain or in or around the cochlea, a vascular structure such as a coronary artery or cerebral artery, or into the cerebral spinal fluid (CSF) or into a reservoir that is in communication with the CSF or the vitreous.

In some embodiments, the subject drug delivery system may be injected directly into the heart, injected or implanted intra-arterially (coronary arteries), or delivered through a catheter to the region of a myocardial infarct.

In some embodiments, the subject drug delivery system may be injected directly into the brain, injected or implanted intra-arterially (typically carotid, cerebral or vertebral I arteries), or delivered through a catheter to the region of an infarct (stroke).

A catheter used to deliver the subject drug delivery system may be combined with a device used to perform a mechanical embolectomy/thrombectomy or stent placement.

The subject drug delivery system may be administered, e.g. after an embolectomy/thrombectomy or stent placement, as a bolus, or may be infused continuously to the region of interest over a period of 0.1 minute to 30 days, 0.1-10 minutes, 10-20 minutes, 20-40 minutes, 40-60 minutes, 1-2 hours, 2-3 hours, 3-4 hours, 4-5 hours, 5-6 hours, 6-8 hours, 8-10 hours, 10-12 hours, 12-18 hours, 18-24 hours, 1-2 days, 2-3 days, 3-4 days, 4-5 days, 5-6 days, 6-7 days, 1-2 weeks, 2-3 weeks, or about 3-4 weeks.

A subject drug delivery system may extend the amount of time that the drug remains in the body. For example, a drug delivery system may provide therapeutic levels of the drug for at least about 2 weeks, at least about 4 weeks, at least about 6 weeks, at least about 8 weeks, at least about 3 months, at least about 4 months, at least about 5 months, at least about 6 months, at least about 7 months, at least about 8 months, at least about 9 months, at least about 10 months, at least about 11 months, at least about 1 year, at least about 1.5 years, at least about 2 years, at least about 3 years, at least about 4 years, about 1-6 months, about 6-12 months, about 12-18 months, about 18-24 months, about 24-36 months, up to about 2 years, up to about 3 years, up to about 4 years, up to about 5 years, or up to about 10 years. The drug delivery system may be injected, implanted, or changed at a time in any of the ranges above.

In some embodiments, a subject drug delivery system may be administered to a mammal, such as a human being, to treat a condition or disease affecting the choroid or retina, such as Age-related Macular Degeneration, Retinal Artery Occlusion, Retinal Vein Occlusion, Retinal Detachment, Central Serous, Chorioretinopathy, Diabetic Retinopathy, Macular Telangiectasia, Familial Exudative Vitreoretinopathy, Retinopathy of Prematurity, Vitreomacular Traction, Macular Hole/Pucker, Ocular Trauma, Pathologic Myopia, Uveitis (serpiginous choroidopathy, sympathetic ophthalmia, birdshot retinochoroidopathy, Acute Multifocal Placoid Pigment Epitheliopathy (AMPPE), Behcet's Disease, Sarcoidosis, Vogt-Koyanagi-Harada's Disease (VKH)), Oculocutaneous albinism, Retinitis Pigmentosa (RP), Choroideremia, Leber's Congenital Amaurosis (LCA), Usher Syndrome, Stargardt's Disease, Juvenile X-Linked Retinoschisis, Leber's Hereditary Optic Neuropathy, Best Disease, Achromatopsia, Cone-Rod Dystrophies, Gyrate Atrophy, Juvenile Macular Degeneration, Kearne-Sayre Syndrome, etc., or a combination thereof.

In some embodiments, a subject composition may be administered to a mammal, such as a human being, to treat a condition or disease affecting the optic nerve, such as, a Glaucoma (Primary Open-Angle Glaucoma (POAG), Acute Primary Angle Close Glaucoma (APACG), Chronic Angle Closure Glaucoma, Pigmentary Glaucoma, Pseudoexfoliation Glaucoma, Normal Tension Glaucoma, Pediatric Glaucoma and the secondary glaucomas), Ischemic Optic Neuropathy, Optic Neuritis/Neuromyelitis Optica, Leber's Hereditary Optic Neuropathy, Optic Atrophy, Optic Nerve Edema, Intracranial Hypertension (Pseudotumor Cerebri), etc., or a combination thereof.

In some embodiments, a subject drug delivery system may be administered to or implanted in a mammal, such as a human being, to treat an otic disorder, such as Meniere's Disease, Sensorineural Hearing loss including hearing loss related to, associated with, or caused by ototoxicity, immune-mediated hearing loss, genetic/inherited (including Usher's, Alport's, Waardenburg's) hearing loss, hearing loss related to, associated with, or caused by noise, presbycusis, traumatic hearing loss, hearing loss related to, associated with, or caused by vascular compromise, hearing loss related to, associated with, or caused by infection, etc., or a combination thereof.

In some embodiments, a subject drug delivery system may be administered to or implanted into a mammal, such as a human being, to treat a central nervous system (CNS) disorder, such as Alzheimer's Disease/Dementias, Anoxia, Stroke, Friedreich's Ataxia, Ataxia Telangiectasia, Asperger Syndrome (Autism), Intracranial Hypertension (Pseudotumor Cerebri), Traumatic Brain Injury, concussion, Diabetic Neuropathy, Dystonias, Essential Tremor, Epilepsy, Riley Day Syndrome, Gangliosidoses, Giant Cell Arteritis, Guillain-Barre Syndrome, Huntington Disease, Refsum Disease, Kearne-Sayre Syndrome and other Mitochondrial Myopathies including Leber's Optic Neuropathy, Amyotrophic lateral sclerosis, Multisystem Atrophy, Myasthenia Gravis, Neurologic Complications of AIDS, Neuromyelitis Optica (Devic's Disease), Autoimmune encephalitis/myelitis, Olivopontocerebellar Atrophy, Parkinson's Disease, Peripheral Neuropathies, Pompe Disease, Shaken Baby Syndrome, Tay-Sachs Disease, Wallenburg's syndrome, Vasculitis, etc., or a combination thereof.

Example 1: Solid Phase Synthesis of a Peptide 6-L-MET12 Featuring an Amide Linkage Using methods known in the art, Peptide 6 is linked to a resin at the $NH_2$ terminus, is protected with BOC groups and t-Bu ester groups, and linked to $NH_2$-terminated-PEG at the carboxylic acid terminus to provide Resin-L-K(Boc)-K(Boc)-E(tBu)-F-L-G-G-D(tBu)-G-V-$CO_2(CH_2—CH_2—O)_n—CH_2—CH_2—NH_2$. The nature of the starting materials, and the order of reactions may be modified to improve efficiency and selectivity, and all reactions are conducted using methods known in the art. MET12 is similarly protected. The free amine of the protected Peptide 6 compound and the free acid of the protected MET12 may be coupled by any appropriate peptide coupling method known in the art. Following the coupling reaction, the protected amide can be fully deprotected using TFA or other acid-catalyzed methods know in the art to release the Peptide 6-L-MET12 amide derivative. Different orthogonal protecting group strategies may be employed as necessary, as known in the art, to optimize the efficiency of the overall procedure.

Example 2: Solid Phase Synthesis of a Peptide 6-L-MET12 Featuring an Ester Linkage Using methods known in the art, peptide 6 is linked to a resin at the $NH_2$ terminus, is protected with CBz groups on the free amine groups and benzyl groups on the free acid groups, and is coupled to polyethylene glycol at the carboxylic acid terminus to provide Resin-L-K(Cbz)-K(Cbz)-E(Bn)-F-L-G-G-D(Bn)-G-V-$CO_2(CH_2—CH_2—O)_n—CH_2—CH_2—OH$. The nature of the starting materials and the order of reactions may be modified to improve selectivity, and all reactions are conducted using methods known in the art. MET12 is similarly protected. The free alcohol terminus of the protected Peptide 6 compound and the free acid of the protected MET12 may be coupled by any appropriate ester coupling method known in the art. Following the coupling reaction, the protected ester can be fully deprotected using hydrogenation methods or other debenzylation methods known in the art to release the Peptide 6-L-MET12 ester derivative. Different orthogonal protecting group strategies may be employed as necessary, as known in the art, to optimize the efficiency of the overall procedure.

The following embodiments are specifically contemplated by the inventors:

Embodiment 1. A drug delivery system comprising: a neurotrophic agent, a FAS/FASL inhibitor, a TNF-α/TNFR inhibitor, a mitochondrial peptide, a chemokine inhibitor, or a cysteine-aspartic protease (caspase) or caspase inhibitor; and an optional sustained delivery component.

Embodiment 2. The drug delivery system of Embodiment 1, comprising the neurotrophic agent.

Embodiment 3. The drug delivery system of Embodiment 1, comprising the FAS/FASL inhibitor.

Embodiment 4. The drug delivery system of Embodiment 1, comprising the TNF-α/TNFR inhibitor.

Embodiment 5. The drug delivery system of Embodiment 1, comprising the mitochondrial peptide.

Embodiment 6. The drug delivery system of Embodiment 1, comprising both the neurotrophic agent and the FAS/FASL inhibitor.

Embodiment 7. The drug delivery system of Embodiment 6, wherein the neurotrophic agent and the FAS/FASL inhibitor are covalently bound to one another.

Embodiment 8. The drug delivery system of Embodiment 7, wherein the neurotrophic agent and the FAS/FASL inhibitor are covalently bound to one another via a linking group.

Embodiment 9. The drug delivery system of Embodiment 1, comprising both the neurotrophic agent and the TNF-α/TNFR inhibitor.

Embodiment 10. The drug delivery system of Embodiment 9, wherein the neurotrophic agent and the TNF-α/TNFR inhibitor are covalently bound to one another.

Embodiment 11. The drug delivery system of Embodiment 10, wherein the neurotrophic agent and the TNF-α/TNFR inhibitor are covalently bound to one another via a linking group.

Embodiment 12. The drug delivery system of Embodiment 1, comprising both the neurotrophic agent and the mitochondrial peptide.

Embodiment 13. The drug delivery system of Embodiment 12, wherein the neurotrophic agent and the mitochondrial peptide are covalently bound to one another.

Embodiment 14. The drug delivery system of Embodiment 13, wherein the neurotrophic agent and the mitochondrial peptide are covalently bound to one another via a linking group.

Embodiment 15. The drug delivery system of Embodiment 1, 2, 3, 4, 5, 6, 7, 8, 9, 10, 11, 12, 13, or 14, wherein the neurotrophic agent comprises a CNTF peptide.

Embodiment 16. The drug delivery system of Embodiment 1, 2, 3, 4, 5, 6, 7, 8, 9, 10, 11, 12, 13, 14, or 15, wherein the neurotrophic agent comprises Peptide 6.

Embodiment 17. The drug delivery system of Embodiment 1, 2, 3, 4, 5, 6, 7, 8, 9, 10, 11, 12, 13, 14, 15, or 16, wherein the neurotrophic agent comprises Peptide 21.

Embodiment 18. The drug delivery system of Embodiment 1, 2, 3, 4, 5, 6, 7, 8, 9, 10, 11, 12, 13, 14, 15, 16, or 17, wherein the neurotrophic agent comprises recombinant CNTF.

Embodiment 19. The drug delivery system of Embodiment 1, 2, 3, 4, 5, 6, 7, 8, 9, 10, 11, 12, 13, 14, 15, 16, 17, or 18, wherein the neurotrophic agent comprises BDNF.

Embodiment 20. The drug delivery system of Embodiment 1, 2, 3, 4, 5, 6, 7, 8, 9, 10, 11, 12, 13, 14, 15, 16, 17, 18, or 19, wherein the neurotrophic agent comprises GDNF.

Embodiment 21. The drug delivery system of Embodiment 1, 2, 3, 4, 5, 6, 7, 8, 9, 10, 11, 12, 13, 14, 15, 16, 17, 18, 19, or 20, wherein the FAS/FASL inhibitor comprises FLIP.

Embodiment 22. The drug delivery system of Embodiment 1, 2, 3, 4, 5, 6, 7, 8, 9, 10, 11, 12, 13, 14, 15, 16, 17, 18, 19, 20, or 21, wherein the FAS/FASL inhibitor comprises MET12.

Embodiment 23. The drug delivery system of Embodiment 1, 2, 3, 4, 5, 6, 7, 8, 9, 10, 11, 12, 13, 14, 15, 16, 17, 18, 19, 20, 21, or 22, wherein the FAS/FASL inhibitor comprises ONL1204.

Embodiment 24. The drug delivery system of Embodiment 1, 2, 3, 4, 5, 6, 7, 8, 9, 10, 11, 12, 13, 14, 15, 16, 17, 18, 19, 20, 21, 22, or 23, wherein the FAS/FASL inhibitor comprises FAS apoptotic inhibitory molecule.

Embodiment 25. The drug delivery system of Embodiment 1, 2, 3, 4, 5, 6, 7, 8, 9, 10, 11, 12, 13, 14, 15, 16, 17, 18, 19, 20, 21, 22, 23, or 24, wherein the FAS/FASL inhibitor comprises nucleolar protein 3.

Embodiment 26. The drug delivery system of Embodiment 1, 2, 3, 4, 5, 6, 7, 8, 9, 10, 11, 12, 13, 14, 15, 16, 17, 18, 19, 20, 21, 22, 23, 24, or 25, wherein the FAS/FASL inhibitor comprises DcR1.

Embodiment 27. The drug delivery system of Embodiment 1, 2, 3, 4, 5, 6, 7, 8, 9, 10, 11, 12, 13, 14, 15, 16, 17, 18, 19, 20, 21, 22, 23, 24, 25, or 26, wherein the FAS/FASL inhibitor comprises DcR2.

Embodiment 28. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, or 27, wherein the FAS/FASL inhibitor comprises DcR3.

Embodiment 29. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, or 28, wherein the TNF-α/TNFR inhibitor comprises etanercept.

Embodiment 30. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, or 29, wherein the TNF-α/TNFR inhibitor comprises infliximab.

Embodiment 31. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, wherein the TNF-α/TNFR inhibitor comprises golimumab.

Embodiment 32. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31, wherein the TNF-α/TNFR inhibitor comprises certolizumab.

Embodiment 33. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32, wherein the TNF-α/TNFR inhibitor comprises adalimumab.

Embodiment 34. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33, wherein the TNF-α/TNFR inhibitor comprises R1antTNF.

Embodiment 35. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34, wherein the TNF-α/TNFR inhibitor comprises DMS5540.

Embodiment 36. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35, wherein the TNF-α/TNFR inhibitor comprises TROS.

Embodiment 37. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36, wherein the TNF-α/TNFR inhibitor comprises ATROSAB.

Embodiment 38. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37, wherein the mitochondrial peptide comprises humanin.

Embodiment 39. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38, wherein the mitochondrial peptide comprises a humanin analog.

Embodiment 40. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the mitochondrial peptide comprises s14G-Humanin.

Embodiment 41. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, wherein the mitochondrial peptide comprises MTP101.

Embodiment 42. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41, wherein the sustained delivery component is silica based.

Embodiment 43. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42, wherein the sustained delivery component is porous.

Embodiment 44. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42, wherein the sustained delivery component is non-porous.

Embodiment 45. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44, wherein the neurotrophic agent is covalently attached to the sustained delivery component.

Embodiment 46. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45, wherein the FAS/FASL inhibitor is covalently attached to the sustained delivery component.

Embodiment 47. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46, wherein the TNF-α/TNFR inhibitor is covalently attached to the sustained delivery component.

Embodiment 48. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, or 47, wherein the mitochondrial peptide is covalently attached to the sustained delivery component.

Embodiment 49. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 47, or 48, wherein the neurotrophic agent is not covalently attached to the sustained delivery component.

Embodiment 50. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 47, 48, or 49, wherein the FAS/FASL inhibitor is not covalently attached to the sustained delivery component.

Embodiment 51. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 48, 49, or 50, wherein the TNF-α/TNFR inhibitor is not covalently attached to the sustained delivery component.

Embodiment 52. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, or 52, wherein the mitochondrial peptide is not covalently attached to the sustained delivery component.

Embodiment 53. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, wherein the sustained delivery component is of the type described in U.S. Pat. No. 9,949,922, issued on Apr. 24, 2018 to Jokinen, et al.

Embodiment 54. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, wherein the sustained delivery component is of the type described in United States Patent Application Publication No. 20140057996, published Feb. 27, 2014 by Jokinen, et al.

Embodiment 55. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, wherein the sustained delivery component is of the type described in U.S. Pat. No. 9,603,801, issued on Mar. 28, 2017 to Barnett, et al., Embodiment 56. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, wherein the sustained delivery component is of the type described in U.S. Pat. No. 9,808,421, issued on Nov. 7, 2017, to Ashton et al.

Embodiment 57. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, wherein the sustained delivery component is of the type described in U.S. Pat. No. 9,333,173 issued on May 10, 2016 to Ashton et al.

Embodiment 58. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, wherein the sustained delivery component is of the type described in United States Patent Publication No. 20140271764 published on Sep. 28, 2014 by Ashton, et al.

Embodiment 59. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, or 58, further comprising an oligonucleotide.

Embodiment 60. A drug delivery system comprising an oligonucleotide and a sustained delivery component.

Embodiment 61. The drug delivery system of Embodiment 59 or 60, wherein the oligonucleotide comprises a small interfering RNA (siRNA).

Embodiment 62. The drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59, wherein the neurotrophic agent comprises nerve growth factor (NGF).

Embodiment 63. A method of treating a medical condition comprising administering a drug delivery system of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62 to a mammal in need thereof, wherein the medical condition comprises: 1) an inherited or age-related choroid, retina, or optic nerve disorder or degeneration; 2) an otic disorder; or 3) a neurologic or CNS disorder.

Embodiment 64. The drug delivery system or method of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63, wherein the FAS inhibitor comprises bicyclol.

Embodiment 65. The drug delivery system or method of Embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63, wherein the chemokine inhibitor comprises NR58.3-14-3.

SEQUENCE LISTING

```
Sequence total quantity: 18
SEQ ID NO: 1            moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 1
VGDGGLFEKK L                                                        11
```

-continued

```
SEQ ID NO: 2            moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 2
DGGLG                                                                         5

SEQ ID NO: 3            moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 3
HHIYLGAVNY IY                                                                 12

SEQ ID NO: 4            moltype = AA  length = 12
FEATURE                 Location/Qualifiers
REGION                  1..12
                        note = source = /note="Description of Artificial Sequence:
                         Synthetic peptide"
source                  1..12
                        mol_type = protein
                        organism = synthetic construct
SEQUENCE: 4
HHIYLGATNY IY                                                                 12

SEQ ID NO: 5            moltype = AA  length = 4
FEATURE                 Location/Qualifiers
REGION                  1..4
                        note = source = /note="Description of Artificial Sequence:
                         Synthetic peptide"
source                  1..4
                        mol_type = protein
                        organism = synthetic construct
SEQUENCE: 5
YLGA                                                                          4

SEQ ID NO: 6            moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 6
IYLGA                                                                         5

SEQ ID NO: 7            moltype = AA  length = 5
FEATURE                 Location/Qualifiers
REGION                  1..5
                        note = source = /note="Description of Artificial Sequence:
                         Synthetic peptide"
source                  1..5
                        mol_type = protein
                        organism = synthetic construct
SEQUENCE: 7
YLGAV                                                                         5

SEQ ID NO: 8            moltype = AA  length = 6
FEATURE                 Location/Qualifiers
REGION                  1..6
                        note = source = /note="Description of Artificial Sequence:
                         Synthetic peptide"
source                  1..6
                        mol_type = protein
                        organism = synthetic construct
SEQUENCE: 8
HIYLGA                                                                        6

SEQ ID NO: 9            moltype = AA  length = 6
```

-continued

```
FEATURE                Location/Qualifiers
REGION                 1..6
                       note = source = /note="Description of Artificial Sequence:
                        Synthetic peptide"
source                 1..6
                       mol_type = protein
                       organism = synthetic construct
SEQUENCE: 9
IYLGAV                                                                      6

SEQ ID NO: 10          moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 10
HIYLGAV                                                                     7

SEQ ID NO: 11          moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 11
IYLGAVN                                                                     7

SEQ ID NO: 12          moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 12
HHIYLGA                                                                     7

SEQ ID NO: 13          moltype = AA  length = 7
FEATURE                Location/Qualifiers
REGION                 1..7
                       note = source = /note="Description of Artificial Sequence:
                        Synthetic peptide"
source                 1..7
                       mol_type = protein
                       organism = synthetic construct
SEQUENCE: 13
YLGAVNY                                                                     7

SEQ ID NO: 14          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 14
HHIYLGAV                                                                    8

SEQ ID NO: 15          moltype = AA  length = 8
FEATURE                Location/Qualifiers
REGION                 1..8
                       note = source = /note="Description of Artificial Sequence:
                        Synthetic peptide"
source                 1..8
                       mol_type = protein
                       organism = synthetic construct
SEQUENCE: 15
YLGAVNYI                                                                    8

SEQ ID NO: 16          moltype = RNA  length = 20
FEATURE                Location/Qualifiers
```

-continued

```
misc_feature            1..20
                        note = source = /note="Description of Artificial Sequence:
                         Synthetic oligonucleotide"
source                  1..20
                        mol_type = other RNA
                        organism = synthetic construct
SEQUENCE: 16
gaaacgaact gcacccggat                                                     20

SEQ ID NO: 17           moltype = RNA  length = 19
FEATURE                 Location/Qualifiers
misc_feature            1..19
                        note = source = /note="Description of Artificial Sequence:
                         Synthetic oligonucleotide"
source                  1..19
                        mol_type = other RNA
                        organism = synthetic construct
SEQUENCE: 17
tagcgactaa acacatcaa                                                      19

SEQ ID NO: 18           moltype = AA  length = 4
FEATURE                 Location/Qualifiers
source                  1..4
                        mol_type = protein
                        note = amino acid motif
                        organism = synthetic construct
SEQUENCE: 18
DGGL                                                                      4
```

The invention claimed is:

1. A drug delivery system comprising: a first active pharmaceutical ingredient (API), a second active pharmaceutical ingredient (API), and a sustained delivery component, wherein the first API is a ciliary neurotrophic factor (CNTF) compound, wherein the second API is a FAS/FASL inhibitor, and wherein the first API is covalently bonded to the second API via a linking group.

2. The drug delivery system of claim 1, having about 100 μg to about 1 mg of the first API.

3. The drug delivery system of claim 1, having about 100 μg to about 1 mg of the second API.

4. The drug delivery system of claim 1, wherein the CNTF compound is a peptide.

5. The drug delivery system of claim 1, wherein the CNTF compound is a peptide containing the amino acid sequence of SEQ ID NO: 18 or a salt thereof.

6. A method of treating a medical condition, comprising administering a drug delivery system of claim 1 to a mammal in need thereof, wherein the medical condition comprises an inherited or age-related choroid, retina, or optic nerve disorder or degeneration.

7. The method of claim 6, wherein the medical condition is an inherited or age-related choroid disorder or degeneration.

8. The method of claim 6, wherein the medical condition is an inherited or age-related retina disorder or degeneration.

9. The method of claim 6, wherein the medical condition is an inherited or age-related optic nerve disorder or degeneration.

10. The method of claim 6, wherein the drug delivery system is injected into an eye of the mammal.

11. The method of claim 6, wherein the mammal is a human being.

12. A method of treating a medical condition, comprising administering a drug delivery system of claim 1 to a mammal in need thereof, wherein the medical condition comprises an otic disorder.

13. The method of claim 12, wherein the drug delivery system is injected into a cochlea of the mammal.

14. The method of claim 12, wherein the mammal is a human being.

15. A method of treating a medical condition, comprising administering a drug delivery system of claim 1 to a mammal in need thereof, wherein the medical condition comprises a neurologic or CNS disorder that is not an inherited or age-related choroid, retina, optic nerve disorder or degeneration, or an otic disorder.

16. The method of claim 15, wherein the drug delivery system is injected into a brain of the mammal.

17. The method of claim 15, wherein the drug delivery system is injected into a cerebral artery, or into the cerebral spinal fluid (CSF), or into a reservoir that is in communication with the CSF.

18. The method of claim 15, wherein the medical condition is Alzheimer's disease, a dementia, anoxia, stroke, Friedreich's ataxia, ataxia telangiectasia, Asperger syndrome, autism, intracranial hypertension, pseudotumor cerebri, traumatic brain injury, concussion, diabetic neuropathy, a dystonia, essential tremor, epilepsy, Riley Day syndrome, gangliosidoses, giant cell arteritis, Guillain-Barre syndrome, Huntington disease, Refsum disease, a mitochondrial myopathy, amyotrophic lateral sclerosis, multisystem atrophy, myasthenia gravis, a neurologic complication of AIDS, Devic's disease, autoimmune encephalitis, autoimmune myelitis, olivopontocerebellar atrophy, Parkinson's disease, peripheral neuropathies, Pompe disease, shaken baby syndrome, Wallenburg's syndrome, or vasculitis.

19. The method of claim 15, wherein the mammal is a human being.

* * * * *